US008062649B2

(12) United States Patent
Asmus et al.

(10) Patent No.: US 8,062,649 B2
(45) Date of Patent: *Nov. 22, 2011

(54) HYDROALCOHOLIC COMPOSITIONS THICKENED USING POLYMERS

(75) Inventors: Robert A. Asmus, Hudson, WI (US); Matthew T. Scholz, Woodbury, MN (US)

(73) Assignee: 3M Innovative Properties Company, St Paul, MN (US)

( * ) Notice: Subject to any disclaimer, the term of this patent is extended or adjusted under 35 U.S.C. 154(b) by 456 days.

This patent is subject to a terminal disclaimer.

(21) Appl. No.: 10/463,497

(22) Filed: Jun. 17, 2003

(65) Prior Publication Data

US 2003/0215418 A1 Nov. 20, 2003

Related U.S. Application Data

(62) Division of application No. 08/781,095, filed on Jan. 9, 1997, now Pat. No. 6,582,711.

(51) Int. Cl.
*A01N 25/00* (2006.01)
*A61K 31/74* (2006.01)
*A61K 47/48* (2006.01)
*A61K 31/045* (2006.01)

(52) U.S. Cl. .................. 424/405; 424/78.17; 424/78.18; 514/724; 523/122

(58) Field of Classification Search ............... 424/78.17, 424/78.18, 78.35, 405; 523/122; 514/57, 514/724

See application file for complete search history.

(56) References Cited

U.S. PATENT DOCUMENTS

| | | | |
|---|---|---|---|
| 2,054,989 A | 9/1936 | Moore | 167/58 |
| 2,153,143 A | 4/1939 | Figg, Jr. et al. | 87/5 |
| 2,678,902 A | 5/1954 | Mehaffey | 167/91 |
| 3,131,152 A | 4/1964 | Klausner | 252/305 |
| 3,131,153 A | 4/1964 | Klausner | 252/305 |
| 3,395,214 A | 7/1968 | Mummert | 424/47 |
| 3,415,939 A | 12/1968 | Minton | 424/357 |
| 3,709,437 A | 1/1973 | Wright | |
| 3,770,648 A | 11/1973 | Mackles | |
| 3,824,303 A | 7/1974 | Lanzet | |
| 3,840,465 A | 10/1974 | Knowles et al. | 252/90 |
| 3,928,558 A | 12/1975 | Cheesman et al. | |
| 3,962,150 A | 6/1976 | Viola | |
| 4,006,218 A | 2/1977 | Sipos | 424/54 |
| 4,199,564 A | 4/1980 | Silver et al. | 421/80 |
| 4,202,881 A | 5/1980 | Gross et al. | 424/70 |
| 4,228,277 A | 10/1980 | Landoll | |
| 4,254,104 A | 3/1981 | Suzuki | 424/170 |
| 4,311,695 A | 1/1982 | Starch | |
| 4,440,653 A | 4/1984 | Briscoe et al. | |
| 4,454,060 A | 6/1984 | Lai et al. | |
| 4,464,293 A | 8/1984 | Dobrin | 252/547 |
| 4,478,853 A | 10/1984 | Chaussee | 424/358 |
| 4,485,089 A | 11/1984 | Leipold | |
| 4,501,834 A | 2/1985 | Su | 524/28 |
| 4,511,486 A | 4/1985 | Shah | |
| 4,542,012 A | 9/1985 | Dell | 424/28 |
| 4,559,226 A | 12/1985 | Fogel et al. | |
| 4,567,038 A | 1/1986 | Ciaudelli et al. | |
| 4,584,189 A | 4/1986 | Leipold | |
| 4,584,192 A | 4/1986 | Dell et al. | 424/81 |
| 4,613,592 A | 9/1986 | Benzoni | |
| 4,666,896 A | 5/1987 | Warner, Jr. et al. | |
| 4,671,957 A | 6/1987 | Holtshousen | 424/80 |
| 4,683,004 A | 7/1987 | Goddard | |
| 4,695,453 A | 9/1987 | Tuominen et al. | 424/81 |
| 4,719,239 A | 1/1988 | Muller et al. | 514/23 |
| 4,752,612 A | 6/1988 | Saito et al. | 514/420 |
| 4,772,592 A | 9/1988 | Benzoni | |
| 4,775,529 A | 10/1988 | Sequeira et al. | |
| 4,806,262 A | 2/1989 | Snyder | 252/90 |
| 4,826,828 A | 5/1989 | Wilmott et al. | |
| 4,831,023 A | 5/1989 | Garlen et al. | |
| 4,839,166 A | 6/1989 | Grollier et al. | |
| 4,839,167 A | 6/1989 | Yamamoto et al. | 424/71 |
| 4,857,302 A | 8/1989 | Decker, Jr. et al. | |
| 4,883,660 A | 11/1989 | Blackman et al. | |
| 4,897,262 A | 1/1990 | Nandagiri et al. | |
| 4,906,459 A | 3/1990 | Cobb et al. | |
| 4,915,934 A | 4/1990 | Tomlinson | 424/45 |
| 4,931,282 A | 6/1990 | Asmus et al. | 424/448 |
| 4,956,170 A | 9/1990 | Lee | 424/81 |
| 4,957,908 A | 9/1990 | Nelson | 514/55 |
| 4,963,535 A | 10/1990 | Sebag et al. | |

(Continued)

FOREIGN PATENT DOCUMENTS

AU        B-72440/87        11/1987

(Continued)

OTHER PUBLICATIONS

Yalpani, *Polysaccharides Synthesis, Modifications and Structure/Property Relations*, Elsevier Science Publishers B.V., Amsterdam, The Netherlands, Title page, Publication page, and pp. 114-117 (1988).
Gilbert et al., "Cationic antiseptics: diversity of action under a common epithet," Journal of Applied Microbiology, 2005; 99: 703-715.
Ventullo et al., "Adaptation of Aquatic Microbial Communities to Quaternary Ammonium Compounds," *Applied and Environmental Microbiology*, Feb. 1986, p. 356-361.
Data Sheet of Klucel® hydroxypropylcellulose,obtained from the internet on Jan. 5, 2005 <http://www.herc.com/aqualon/personal_care/pc_prod_data/pc_lucel.html>.
de Bruin, Hydrophobically Modified cellulose Ether for Personal Care, SÖFW Journal, 120$^{th}$ year, 15/1994, pp. 944-947.
Domsch, *Die kosmetischen Präparate* [Preparations in Cosmetics], vol. 11, 4$^{th}$ Edition, Verlag fur die chem., Industrie, 1992, p. 57 + p. 118, formulation RX2.114.

(Continued)

*Primary Examiner* — Johann Richter
*Assistant Examiner* — Andriae M Holt
(74) *Attorney, Agent, or Firm* — Thomas M. Spielbauer

(57) ABSTRACT

An antimicrobial hydroalcoholic composition comprising hydroalcoholic solvent system comprising a lower alcohol and water in a weight ratio of at least about 50:50; a thickener system comprising at least one cationic or nonionic polymeric thickener that is solid at ambient temperature; and a secondary antimicrobial agent.

74 Claims, 1 Drawing Sheet

U.S. PATENT DOCUMENTS

| | | | |
|---|---|---|---|
| 4,981,678 A | 1/1991 | Tomlinson | 424/45 |
| 4,983,377 A | 1/1991 | Murphy et al. | |
| 5,100,658 A * | 3/1992 | Bolich et al. | 424/70.12 |
| 5,104,646 A | 4/1992 | Bolich, Jr. et al. | |
| 5,120,716 A | 6/1992 | Miyazawa et al. | 514/23 |
| 5,128,123 A | 7/1992 | Brewster et al. | 424/65 |
| 5,149,719 A | 9/1992 | Ferber et al. | 514/772 |
| 5,164,107 A | 11/1992 | Khan et al. | 252/106 |
| 5,167,950 A | 12/1992 | Lins | 424/47 |
| 5,180,061 A | 1/1993 | Khan et al. | 206/570 |
| 5,180,584 A | 1/1993 | Sebag et al. | 424/401 |
| 5,204,099 A | 4/1993 | Barbier et al. | |
| 5,223,261 A | 6/1993 | Nelson et al. | 424/443 |
| 5,225,473 A | 7/1993 | Duan | 524/388 |
| 5,232,691 A | 8/1993 | Lemole | 424/78.02 |
| 5,288,486 A | 2/1994 | White | |
| 5,290,555 A | 3/1994 | Guthauser et al. | |
| 5,298,182 A | 3/1994 | Tsao et al. | |
| 5,298,242 A | 3/1994 | Vanlerberghe et al. | 424/78.36 |
| 5,300,284 A | 4/1994 | Wiechers et al. | |
| 5,314,684 A | 5/1994 | Horoschak et al. | |
| 5,334,388 A | 8/1994 | Hoang et al. | 424/402 |
| 5,362,484 A | 11/1994 | Wood et al. | 424/70 |
| 5,409,966 A | 4/1995 | Duan et al. | 522/152 |
| 5,456,745 A | 10/1995 | Roreger et al. | |
| 5,484,597 A | 1/1996 | Slavtcheff et al. | 424/401 |
| 5,494,533 A | 2/1996 | Woodin, Jr. et al. | |
| 5,512,199 A | 4/1996 | Khan et al. | 252/106 |
| 5,547,662 A | 8/1996 | Khan et al. | |
| 5,549,888 A | 8/1996 | Venkateswaran | |
| 5,567,428 A | 10/1996 | Hughes | |
| 5,585,092 A | 12/1996 | Trandai et al. | 424/65 |
| 5,612,324 A * | 3/1997 | Guang Lin et al. | 514/162 |
| 5,626,853 A | 5/1997 | Bara et al. | 424/401 |
| 5,629,006 A | 5/1997 | Hoang et al. | |
| 5,635,469 A | 6/1997 | Fowler et al. | |
| 5,662,893 A | 9/1997 | George | |
| 5,690,921 A | 11/1997 | Lang et al. | |
| 5,693,255 A | 12/1997 | Okamoto et al. | |
| 5,733,535 A | 3/1998 | Hollingshead et al. | |
| 5,756,077 A | 5/1998 | Syed et al. | |
| 5,767,161 A | 6/1998 | Stroppolo et al. | |
| 5,776,430 A | 7/1998 | Osborne et al. | |
| 5,799,841 A | 9/1998 | Wirt | 222/571 |
| 5,824,320 A | 10/1998 | Rouillard et al. | |
| 5,856,347 A | 1/1999 | Hashiguchi et al. | |
| 5,897,031 A | 4/1999 | Wirt et al. | 222/179 |
| 5,908,619 A | 6/1999 | Scholz | |
| 5,935,587 A | 8/1999 | Cauwet et al. | |
| 5,951,993 A | 9/1999 | Scholz et al. | |
| 5,972,356 A | 10/1999 | Peffly et al. | |
| 5,980,876 A | 11/1999 | Peffly | |
| 6,019,997 A | 2/2000 | Scholz et al. | |
| 6,086,856 A | 7/2000 | Saferstein et al. | |
| 6,090,395 A | 7/2000 | Asmus et al. | 424/401 |
| 6,117,440 A | 9/2000 | Suh et al. | |
| 6,183,766 B1 | 2/2001 | Sine et al. | |
| 6,333,039 B1 | 12/2001 | Fendler et al. | |
| 6,352,701 B1 | 3/2002 | Scholz et al. | |
| 6,383,997 B1 | 5/2002 | McManus | |
| 6,423,329 B1 | 7/2002 | Sine et al. | |
| 6,472,356 B2 | 10/2002 | Narula et al. | |
| 6,534,069 B1 | 3/2003 | Asmus et al. | |
| 6,562,360 B2 | 5/2003 | Scholz et al. | |
| 6,582,711 B1 | 6/2003 | Asmus et al. | |
| 6,610,315 B2 | 8/2003 | Scholz et al. | |
| 6,623,744 B2 | 9/2003 | Asmus et al. | |
| 7,081,246 B2 | 7/2006 | Asmus et al. | |
| 7,566,460 B2 | 7/2009 | Asmus et al. | |
| 7,651,990 B2 | 1/2010 | Asmus | |
| 2002/0040046 A1 | 4/2002 | Patel et al. | |
| 2002/0127253 A1 | 9/2002 | Scholz et al. | |
| 2002/0142018 A1 | 10/2002 | Scholz et al. | |
| 2002/0160029 A1 | 10/2002 | Asmus et al. | |
| 2003/0211066 A1 | 11/2003 | Scholz et al. | |
| 2003/0215418 A1 | 11/2003 | Asmus et al. | |
| 2004/0071748 A1 | 4/2004 | Asmus et al. | |
| 2004/0219227 A1 | 11/2004 | Modak et al. | |
| 2004/0247685 A1 | 12/2004 | Modak et al. | |
| 2006/0018847 A1 | 1/2006 | Kroepke et al. | |
| 2006/0121071 A1 | 6/2006 | Asmus et al. | |
| 2006/0263396 A1 | 11/2006 | Asmus et al. | |
| 2006/0281663 A1 | 12/2006 | Asmus | |
| 2006/0292086 A1 | 12/2006 | Curtis | |
| 2007/0148101 A1 | 6/2007 | Snyder et al. | |
| 2008/0108704 A1 | 5/2008 | Asmus et al. | |
| 2009/0326076 A1 | 12/2009 | Asmus | |

FOREIGN PATENT DOCUMENTS

| | | |
|---|---|---|
| DE | 34 16 777 A1 | 11/1985 |
| DE | 3716381 | 11/1987 |
| DE | 36 32 030 A1 | 3/1988 |
| DE | 3803022 | 8/1988 |
| DE | 3827561 | 12/1989 |
| EP | 0 014 502 A1 | 8/1980 |
| EP | 0 117 889 | 9/1984 |
| EP | 0 159 167 A2 | 10/1985 |
| EP | 0 159 167 A3 | 10/1985 |
| EP | 0 213 527 | 3/1987 |
| EP | 0 223 681 A1 | 5/1987 |
| EP | 0 260 641 A2 | 3/1988 |
| EP | 0 289 160 A1 | 4/1988 |
| EP | 0 327 379 A2 | 8/1989 |
| EP | 0 381 618 A2 | 8/1990 |
| EP | 0 451 949 A1 | 10/1991 |
| EP | 0 522 624 A1 | 1/1993 |
| EP | 0 689 767 A2 | 1/1996 |
| EP | 0 745 389 A1 | 12/1996 |
| EP | 0 990 412 | 4/2000 |
| EP | 0 963 158 B1 | 7/2003 |
| EP | 1811013 | 7/2007 |
| FR | 788 811 | 10/1935 |
| FR | 77 31410 | 10/1977 |
| FR | 2 406 438 | 5/1979 |
| GB | 1 527 781 | 10/1978 |
| JP | 58-39620 | 3/1983 |
| JP | 61-500357 | 3/1986 |
| JP | 61-207326 | 9/1986 |
| JP | 61-507326 | 9/1986 |
| JP | 62-106012 | 5/1987 |
| JP | 63-183520 | 7/1988 |
| JP | 1-305043 | 12/1989 |
| JP | 2-218605 | 8/1990 |
| JP | 06279268 | 10/1994 |
| JP | 6-327750 | 11/1994 |
| JP | 07285808 | 10/1995 |
| JP | 8-12571 | 1/1996 |
| JP | 80 92 078 | 4/1996 |
| JP | 11349418 | 12/1999 |
| WO | WO 85/01876 A1 | 5/1985 |
| WO | WO85/03510 | 8/1985 |
| WO | 93/00089 | 1/1993 |
| WO | WO 93/00089 | 1/1993 |
| WO | WO 93/07903 | 4/1993 |
| WO | WO 93/21899 | 11/1993 |
| WO | WO 93/25624 A1 | 12/1993 |
| WO | WO 94/13354 | 6/1994 |
| WO | WO 9501384 A1 * | 1/1995 |
| WO | WO 95/03772 | 2/1995 |
| WO | WO 97/00667 | 1/1997 |
| WO | WO 97/00668 | 1/1997 |
| WO | WO 97/48321 | 12/1997 |
| WO | WO 97/48322 | 12/1997 |
| WO | WO 99/20250 | 4/1999 |

OTHER PUBLICATIONS

Fiedler, *Lexicon der Hilksstoffe für Pharmazie, Kosmetik und angrensende Gebiete* [Encyclopedia of additives in the pharmaceutical, cosmetic and related fields], 4$^{th}$ edition (1996), Publishing House Editio Cantar Aulendorf, Title page, and pp. 330, 946, and 1248.

Product Information regarding CEKAQUAT SC230M of the company National Starch, Feb. 2001, 5 pages.

U.S. Appl. No. 10/400,597, filed Mar. 27, 2003, Scholz et al.

U.S. Appl. No. 11/340,778, filed Jan. 26, 2006, Asmus et al.

U.S. Appl. No. 11/151,563, filed Jun. 13, 2005, Asmus.

U.S. Appl. No. 11/492,635, filed Jul. 25, 2006, Asmus et al.
U.S. Appl. No. 11/928,966, filed Oct. 30, 2007, Asmus.
Quadir et al., "A Comparative Study of Current Superdisintegrants," *Pharmaceutcal Technology*, Oct. 1, 2006 [available online, retrieved on Oct. 29, 2007]. Retrieved from the Internet:<URL:http://license.icopyright.net/user/viewFreeUse.act?fuid=NTMxODMx>; 4 pgs. (Exhibit A).
"Mutchler Chemicals Website" datasheet [online]. Mutchler, Inc., Harrington Park, New Jersey, 2006 [retrieved on Oct. 5, 2007]. Retrieved from the Internet<URL:http://www.mutchlerchem.com/manufacturers_basf.html>; 4 pgs. (Exhibit B).
Bühler, "Kollidon® Polyvinylpyrrolidone for the pharmaceutical industry," Product Information Manual, 4$^{th}$ Edition, BASF Aktiengesellschaft, Germany, Mar. 1998. 288 pgs. (Exhibit C).
Sivadasan and Somasundaran, "Polymer-Surfactant Interactions and the Association Behavior of Hydrophobically Modified Hydroxyethylcellulose," *Colloids and Surfaces*, 1990;49:229-239.
"Functional Gel", Aizo Yamauchi and Kazushi Hirokawa, Kyoritsu Publishing Co. Jun. 15, 1990, pp. 13-14 (Japanese only).
"Ciba® SALCARE® Liquid Dispersion Polymers," Ciba Specialty Chemicals, Mar. 2003: 28 pgs.
"SEPIGEL 305 Thickening Agent for Cream Gels and Emulsions", Mar. 1995, pp. 1-24 (Exhibit A).
*Scientific Encyclopedia*, 8$^{th}$ Edition, 1995, Von Nostrand Reinhold, 4 pgs. (Exhibit B).
*Dictionary of Scientific and Technical Terms*, 5$^{th}$ Edition, 1994, McGraw-Hill, 3 pgs. (Exhibit C).
U.S. Appl. No. 12/552,126, filed Sep. 1, 2009; and entitled "Foamable Alcohol Compositions, Systems and Methods of Use".
Biosis Abstract 80:188 400, Abstract of *Zentralbl Bakteriol Parasitenkd Infektionskr Hgy Erst Abt Orig Reihe B Hvg Krankaenhaushvg Betriebshyg Praev Med*, 168, pp. 5-6 (1979).
Biosis Abstract 86:434 601, Abstract *Hvg. Med.*, 11, pp. 238-241 (1986).
Bulletin No. 51-0001-259, Speciality Chemicals of ICI America of Wilmington, DE.
J.L. Cohen et al., "Penetration of 5-Fluorouracil in Excised Skin", *The J. of Investigative Dermatology*, 62, pp. 507-509 (1974).
CTFA Cosmetic Ingredient Handbook, Published by The Cosmetic, Toiletry and Fragrance Association, Inc., pp. 37,64-65,78, 81 (1988).
G.M. Eccleston, "Application of Emulsion Stability Theories to Mobile and Semisolid O/W Emulsions", *Cosmetics & Toiletries*, 101, pp. 73-92 (1986).
G.M. Eccleston, "Influence of long chain alcohols (or acids) and surfactants on the stabilities and consistencies of cosmetic lotions and creams", *Cosmetics and Toiletries*. 92. pp. 21-28 (1977).
E.D. Goodard et al., "Novel gelling structures based on polymer/surfactant systems", *J. Soc. Cosmet. Chem.*, 42, pp. 19-34 (1991).
P.B. Price, "Reevaluation of Ethyl Alcohol as a Germicide", *Archives of Surgery*, pp. 492-502 (Undated).
R.B. Stoughton, "Vasoconstrictor Activity and Percutaneous Absorption of Glucocorticosteroids", *Arch. Derm.*, 92. pp. 753-756 (1969).
"Textbook of Polymer Science", F.W. Billmeyer, Ed.; Wiley-Interscience, NY; 2$^{nd}$ Edition; pp. 84-85 (1971).
Guy et al., "Chapter 3: Selection of Drug Candidates for Transdermal Drug Delivery," Transdermal Drug Delivery Developmental Issues and Research Initiatives, Hadgraft et al., eds., Marcel Dekker, Inc., New York, Title page, publication page and pp. 59-81 ((1989).
Smith et al., eds., *Percutaneous Penetration Enhancers*, CRC Press, Boca Raton, FL., Title page, publication page and table of contents only, 6 pages (1995).
Yamashita et al., "Surfactants, Polymeric (Overview)," *Polymeric Materials Encyclopedia*, vol. 10, Salamone, ed., CRC Press, Boca Raton, FL., Title page, publication page, and pp. 8195-8201 (1996).
Notice of Opposition by BODE Chemie against EP Patent No. 0963158; May 26, 2004; 15 pgs, in German. English Translation of Notice of Opposition by BODE Chemie against EP Patent No. 0963158; May 26, 2004; 7 pgs.
Response to Notice of Opposition for EP Patent No. 963158; Jan. 5, 2005; 23 pgs.
D1—EP A 223681.
D2—US 5,167,950.
D3—Data Sheet of Klucel® hydroxypropylcellulose, obtained from the internet on Jan. 5, 2005 <http://www.herc.com/aqualon/personal_care/pc_prod_data/pc_lucel.html>. Annex 3, Previously submitted on 1449 Dated Sep. 7, 2007.
Summons to attend Oral Proceedings pursuant to Rule 71(1)EPC; Jan. 12, 2006; 7 pgs.
Brief filed by the Opponent, Beiersdorf AG; Apr. 10, 2006; 42 pgs, in German. English Translation of the Brief filed by the Opponent, Beiersdorf AG; Apr. 10, 2006; 32 pgs.
D4—Request for entry into the regional phase before the EPO as designated or elected office, of the patent in suite EP0963158, dated Jul. 6, 1999; 5 pgs.
D5—Reply of the patentee's representative to the communication according to Rule 51(4) of Jan. 7, 2003; approval of the text for grant of the patent in suit EP0963158, including replacement pages; 18 pgs.
D6—Reply of the patentee's representative to the communication according to Rule 51(6) of May 12, 2003; translation of the claims for EP0963158; 11 pgs.
D7—de Bruin, Hydrophobically Modified cellulose Ether for Personal Care, SÖFW Journal, 120$^{th}$ year, 15/1994, pp. 944-947.
D8—EP 689767.
D9—A. Domsch, "Die Kosmetischen Praparate," Vol. II, 4thy Edition, 1992, pp. 57 and 118, receipe RZ2.114. English Translation of p. 57 of reference D9 enclosed with Opponent's Brief of Apr. 10, 2006.
D10—Comparative tests of the recipes on p. 13, example 1 of the patent in suit, from opposition of EP Patent No. 963158; 1 pg. Apr. 10, 2006.
D11—Product Information of CELQUAT SC230M of National Starch, 5 pgs.
D12—Email of Mr. Wendt of National Starch of Apr. 9, 2006 from opposition of EP Patent No. 0963158; 1 pg. English Translation of Email of Mr. Wendt of National Starch of Apr. 9, 2006 from opposition of EP Patent No. 0963158; 1 pg.
Communication to the European Patent Office in preparation of Oral Hearings for the Opposition against EP Patent No. 0963158; Apr. 10, 2006; 9 pgs.
Communication to the European Patent Office in preparation of Oral Hearings for the Opposition against EP Patent No. 0963158; May 24, 2006; 16 pgs.
Annex 4—Photograph showing a Brookfield Spindles Picture, T spindle (left) and an LVT spindle #3 (right); 1 pg. (D14).
Annex 5—US Published application No. US 2006/0018847.
Test Report regarding viscosity, 6 pgs.; May 31, 2006.
Opponent Brief dated Jun. 1, 2006 in German, 8 pgs. English Translation of Opponent Brief dated Jun. 1, 2006.
D13a—Viscosity measurements of the composition of example 1 of the patent in suit, from opposition of EP Patent No. 0963158; Brookfield Engineering Labs, Inc.; 2 pgs., Jun. 1, 2006.
D13b—Viscosity measurements of the composition of example 1 of the patent in suit, from opposition of EP Patent No. 0963158; Brookfield Engineering Labs, Inc.; 4 pgs., Jun. 1, 2006.
Minutes of First Oral Proceedings dated Jun. 8, 2006, 2 pgs.
Decision rejecting opposition against EP Patent No. 0963158; Jul. 7, 2006; 17 pgs.
Notice of Appeal filed by Beiersdorf AG, Sep. 7, 2006, in German; 15 pgs. English Translation of Notice of Appeal filed by Beiersdorf AG, Sep. 7, 2006; 14 pgs.
D16—Fiedler, *Lexicon der Hilksstoffe für Pharmazie, Kosmetik und angrensende Gebiete* [*Encyclopedia of additives in the pharmaceutical, cosmetic and related fields*], 4$^{th}$ edition (1996), Publishing House Edition Cantar Aulendorf, Title page, and pp. 330, 946, and 1248.
Reply to Notice of Appeal by the Patentee; Jan. 24, 2007, 14 pgs.
Second Summons to Oral Proceedings. Sep. 2, 2008; 2 pgs.
Minutes of Second Oral Proceedings dated Dec. 11, 2008, 2 pgs.
Brief filed by the Opponent in German, Nov. 10, 2008, 10 pgs. English Translation of the Brief dated Nov. 10, 2008, 6 pgs.
D17—English Translation of the Expert Opinion regarding the results of corresponding viscosity measurements, 2 pgs.
Decision on Appeal dated Mar. 16, 2009, 33 pgs.

"Acrylamide," Wikipedia Reference, [online]. [retrieved on Aug. 10, 2010]. Retrieved from the Internet:<URL:http://en.wikipedia.org/wiki/acrylamide>;11 pgs.

Dallal and Rocafort, "Chapter 5—Hair Styling/Fixative Products," *Hair and Hair Care*, Helene Curtis, Rolling Meadows, IL, New York, NY, 1997; table of contents and pp. 135-138.

U.S. Appl. No. 12/878,786, filed Sep. 9, 2010, Asmus et al.
U.S. Appl. No. 12/878,793, filed Sep. 9, 2010, Asmus et al.
U.S. Appl. No. 12/878,883, filed Sep. 9, 2010, Asmus et al.

* cited by examiner

HYDROALCOHOLIC COMPOSITIONS THICKENED USING POLYMERS

CROSS REFERENCE TO RELATED APPLICATIONS

This application is a division of U.S. patent application Ser. No. 08/781,095, filed Jan. 9, 1997 now U.S. Pat. No. 6,582,711.

FIELD OF THE INVENTION

The present invention relates to compositions useful as surgical hand preparations and antimicrobial hand lotions. More specifically the invention relates to stable hydroalcoholic compositions thickened using nonionic or cationic polymers.

BACKGROUND OF THE INVENTION

Control of nosocomial infection and exposure to infectious disease is of paramount concern to doctors, nurses, and clinicians who work in hospitals and surgery centers. One of the most effective methods for controlling infection is regimented hand disinfection before and possibly after each patient contact and particularly before and after each surgical procedure. Hand disinfection is generally accomplished using antimicrobial soaps with water. These soaps are usually formulated to include either povidone-iodine (usually 7.5% by weight) or chlorhexidine digluconate (CHG) (usually 2% or 4% by weight) as the active antimicrobial agent. In addition, these formulated soaps may contain surfactants and possibly low levels of humectants such as glycerin.

Hand disinfection is also accomplished using presurgical scrub replacements. These are used instead of the soap and water scrub. Presurgical scrub replacements ideally achieve bacterial kill equal to or better than a traditional soap and water scrub and in a shorter period of time. Additionally, they maintain or improve the skin's natural barrier to microbial and chemical contamination while providing acceptable tactile properties. Examples of presurgical scrub replacements include hydroalcoholic gels which generally include high levels of either ethanol or isopropanol as the disinfecting agent and also include a thickener and optionally a humectant (e.g., glycerin).

To date, thickeners used in hydroalcoholic gels have been based primarily on anionic polymers such as polyacrylic acid (sold under the tradename "CARBOPOL" by B F Goodrich Specialty Polymers and Chemicals Division of Cleveland, Ohio). See, for example, U.S. Pat. Nos. 4,956,170 (Lee) and 5,167,950 (Lins). These compositions are generally incompatible with cationic compounds such as chlorhexidine gluconate. There are a few reports of nonionic and cationic-polymeric thickeners being used as well. See, for example, U.S. Pat. No. 4,478,853 (Chausee) and International Publication No. WO 93/007903 (Deckner). These hydroalcoholic compositions have relatively low levels of alcohol, generally too low to provide rapid and effective antimicrobial activity.

U.S. Pat. No. 5,512,199 (Khan) discloses a hydroalcoholic wipe composition, incorporating nonionic and cationic polymeric emollients or humectants. These compositions have very low viscosities, too low to be used as a lotion. U.S. Pat. Nos. 4,915,934 (Tomlinson) and 4,981,698 (Tomlinson) provide hydroalcoholic biocidal compositions incorporating low molecular weight polymeric emollients such as polyglycerol and polyvinyl pyrrolidone. These polymers do not provide adequate thickening in hydroalcoholic lotions.

In other hydroalcoholic systems, such as those described in U.S. patent application Ser. Nos. 08/493,714 and 08/493,695 (both of which were filed on Jun. 22, 1995 and assigned to 3M Company), nonionic, anionic, cationic, or zwitterionic emulsifiers are used as thickeners for a wide range of concentrations of alcohol, without the need for a polymeric thickener such as polyacrylic acid. Although these systems are highly desirable, other high viscosity hydroalcoholic compositions useful as an antimicrobial lotion, for example, are still needed.

SUMMARY OF THE INVENTION

This invention provides compositions useful as products for skin disinfection such as presurgical hand preparations and lotions that are easily washed off hands with water, preferably with no apparent residue. The preferred compositions of this invention, in general, have a very nice feel after both single and multiple applications. Preferred compositions maintain or improve the skin condition after multiple applications with no slimy or abnormal feeling noticed during post application hand washing. When used as a presurgical scrub replacement, this invention achieves bacterial, fungal, and viral kill equal to or better than a traditional soap and water scrub in a shorter period of time while maintaining or improving the skin's natural barrier to microbial and chemical contaminants. Additionally, these compositions are compatible with cationic additives, such as chlordexidine digluconate. The invention overcomes the shortcomings of past compositions by providing a viscous cosmetically elegant lotion that is substantially nontacky and maintains or improves skin condition and is compatible with cationic additives. Further, the composition has a cosmetically elegant feel and may be dispensed as a lotion or as a foam.

One embodiment of the present invention is an antimicrobial hydroalcoholic composition comprising: a hydroalcoholic solvent system comprising a lower alcohol and water in a weight ratio of at least about 50:50; a thickener system comprising at least one cationic polymeric thickener that is solid at ambient temperature; wherein the cationic thickener is selected such that the composition has a viscosity of at least about 10,000 centipoise at 23° C.; wherein the thickener system is present in an amount of at least about 0.5% by weight, based on the total weight of the composition; and a secondary antimicrobial agent.

Another embodiment is an antimicrobial hydroalcoholic lotion comprising: a hydroalcoholic solvent system comprising a lower alcohol and water in a weight ratio of at least about 60:40; a thickener system consisting essentially of one or more nonionic polymeric thickeners, at least one of which is solid at ambient temperature; wherein the one or more polymeric thickeners are selected such that the composition has a viscosity of at least about 4,000 centipoise at 23° C.; and further wherein the thickener system is present in an amount of at least about 0.5% by weight, based on the total weight of the composition; and a secondary antimicrobial agent.

Yet another embodiment of the invention is an antimicrobial hydroalcoholic lotion comprising: a hydroalcoholic solvent system comprising a lower alcohol and water in a weight ratio of at least about 60:40; a thickener system comprising at least one associative polymeric thickener that is solid at ambient temperature; wherein the associative polymeric thickener is selected such that the composition has a viscosity of at least about 4,000 centipoise at 23° C.; wherein the thickener system is present in an amount of at least about 0.5% by weight, based on the total weight of the composition; and a secondary antimicrobial agent.

DEFINITIONS

"Ambient temperature" as used herein refers to the temperature range of about 21-25° C.

"Emollient" as used herein refers broadly to materials which are capable of maintaining or improving the moisture level, compliance, or appearance of the skin when used repeatedly.

"Emulsifier" as used herein is synonymous with "surfactant" and refers to molecules comprising hydrophilic (polar) and hydrophobic (non-polar) regions on the same molecule.

"Emulsion" as used herein refers to a stable dispersion of one liquid in a second immiscible liquid. Emulsion also refers to stable dispersions of a solid in an immiscible liquid wherein the solid was formed by cooling below the freezing point of the solid composition.

"Lotion" means liquid or cream, free of any propellant.

"Polymer" as used herein refers to a natural, modified-natural, or synthetic molecule having repetitive units and a number average molecular weight of at least about 20,000.

"Solvent," "solvent system," or "hydroalcoholic solvent" as used herein refer to the alcohol and water combination in the present invention.

"Stable" as used herein refers to a composition that displays less than or equal to 10% by volume separation after centrifuging at 1545×g for 30 minutes at ambient temperature.

"Surfactant" as used herein is synonymous with "emulsifier," the definition of which is given above.

"Thickener System" as used herein refers to at least one nonionic or cationic polymer that is solid at ambient temperature.

DETAILED DESCRIPTION OF THE INVENTION

Figure 1:
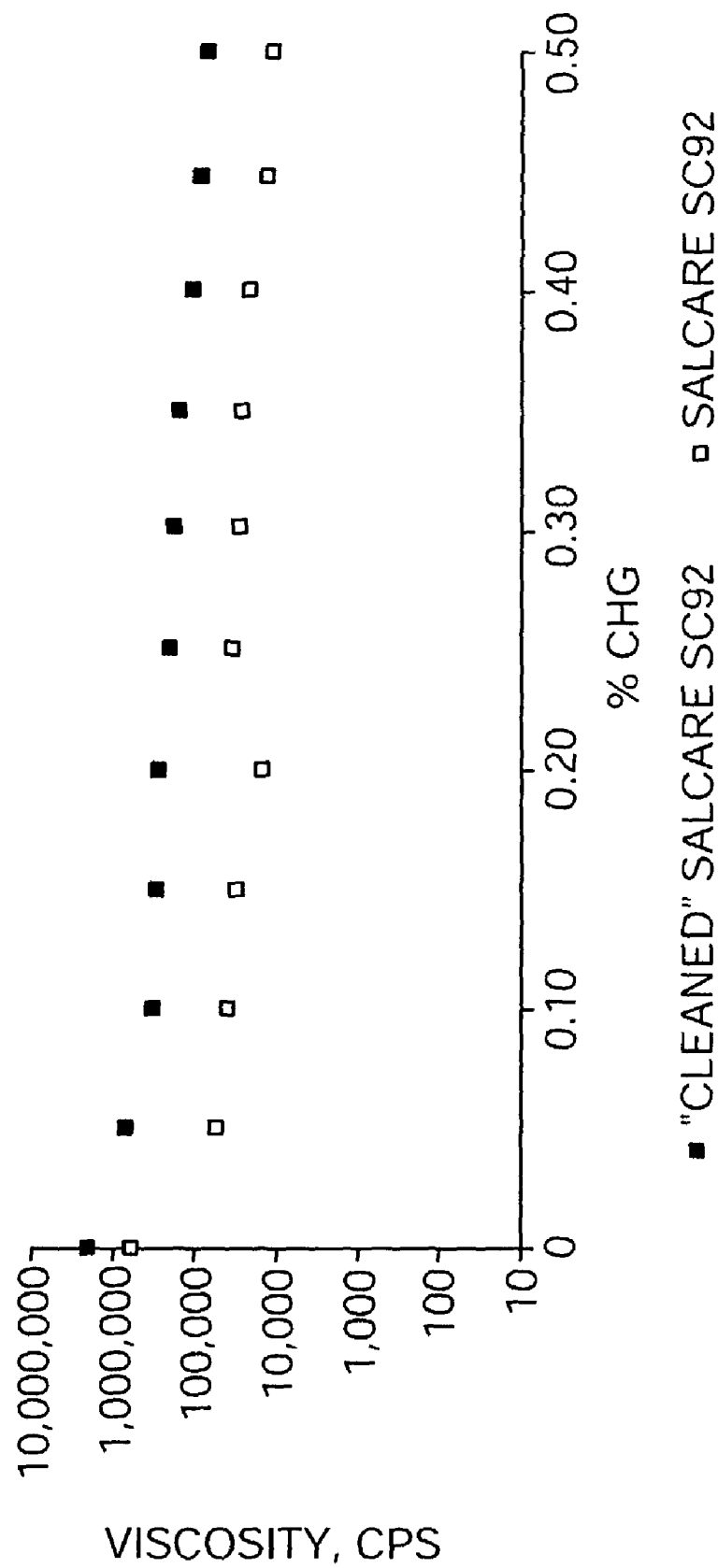
FIG. 1 is a graph of viscosity loss as a function of excess ion concentration.

The invention provides a hydroalcoholic composition comprised of a lower chain alcohol, water, a thickening system, and a secondary antimicrobial agent (i.e., an antimicrobial agent other than the lower alcohol). The thickening system includes at least one nonionic or cationic polymeric thickener (or mixture thereof) that is solid at ambient temperature. Significantly, the polymeric thickeners are capable of thickening a hydroalcoholic solvent system containing a ratio of a lower alcohol to water of about 50:50, and even higher ratios (e.g., 60:40 and above). Such high concentrations of alcohol are important for providing compositions that have highly effective antimicrobial activity and are fast drying.

Furthermore, the compositions of the present invention preferably have a pH of at least about 5, more preferably at least about 5.5, and most preferably at least about 6. The pH is preferably no greater than about 9.5, more preferably no greater than about 8.5, and most preferably no greater than about 8.

Hydroalcoholic Solvent System

The compositions of the present invention include one or more alcohols in combination with water, thereby producing a hydroalcoholic solvent system. The alcohol used in the compositions of the present invention is a lower chain hydrocarbon alcohol (referred to herein as a "lower alcohol"), particularly a C1-C4 alcohol (i.e., an alcohol containing 1-4 carbon atoms). In preferred embodiments, the alcohol is ethanol, 2-propanol (i.e., isopropanol), or n-propanol. In more preferred embodiments, the alcohol is ethanol. Ethanol is a preferred alcohol because it provides quick killing of a broad spectrum of microbes. Furthermore, it has an acceptable odor to health care practitioners and patients.

The lower alcohol to water ratio in the compositions of the present invention is at least about 50:50 by weight (i.e., the lower alcohol is present in an amount of at least about 50 weight percent, and the water is present in an amount of about 50 weight percent, based only on the weight of the water plus the lower alcohol within the composition), and preferably at least about 60:40, by weight. Typically, compositions of the present invention have an alcohol to water ratio of no greater than about 99:1 by weight. Compositions having an alcohol to water ratio within a range of about 50:50 to 95:5 by weight (i.e., 50-95 weight percent alcohol and 5-50 weight percent water, based only on the weight of water plus lower alcohol in the composition) ensure an efficacious immediate bacterial kill, particularly when used in combination with a secondary antimicrobial agent (i.e., an antimicrobial agent other than the lower alcohol). In particularly preferred embodiments, the lower alcohol to water ratio is within a range of about 50:50 to about 85:15, and more preferably about 60:40 to about 75:25. Higher ratios of alcohol to water are used in preferred embodiments containing secondary antimicrobial agents for optimum antimicrobial activity and to ensure the composition is fast drying.

Thickener System

The thickener system useful in this invention affects the cosmetic attributes of the final composition. Preferably, hand preps and lotions of the invention have the following desirable cosmetic attributes. The composition should not result in excessive clumping of glove powder beneath powdered surgical gloves and should not affect the integrity of the glove material. Preferred compositions when applied to the skin and allowed to dry, do not result in balling up when rubbed. The compositions should preferably maintain an acceptable viscosity (e.g., at least about 4000 centipoise) at ambient temperatures (i.e., 21-25° C.), and preferably up to about 35° C. Preferred compositions are stable to heat and cool cycles (heating up to 50° C. or higher and cooling to ambient temperature) as well as freeze/thaw cycles (cooling to −30° C. and warming to ambient temperature). All of these cosmetic attributes are affected by the types and amounts of polymers chosen.

The thickener system of the invention is compatible with the hydroalcoholic solvent system described above in order to provide suitable stability, acceptable cosmetic properties, and appropriate viscosity. Compositions of this invention have a viscosity of at least about 4,000 centipoise (cps), preferably at least about 10,000 cps, more preferably at least about 20,000 cps, even more preferably at least about 50,000 cps, and most preferably at least about 80,000 cps (and even as high as about 500,000 cps or more), at 23° C., measured using a very low shear viscometer such as Brookfield LVDV-I+ viscometer and T spindles with a heliopath adapter. Because certain optional ingredients, such as emollients, may effect the viscosity (either positively or negatively), the measured viscosity is that of the final composition.

The thickener system can be prepared from one or more nonionic or cationic polymers, preferably both nonionic and cationic polymers. Each of these may be chosen from a single class of compounds or from more than one class. Typically, anionic thickeners have been used to thicken hydroalcoholic solvent systems. It was unexpected that nonionic and cationic polymers could also thicken hydroalcoholic solvent systems, particularly those containing high levels of alcohol.

Significantly, thickener systems of the present invention are capable of achieving high viscosities at relatively low total polymer concentrations. The total concentration of nonionic or cationic polymers (or both) present in the thickener system is preferably less than about 10% by weight, more preferably less than about 8% by weight, and most preferably less than about 6% by weight, of the total composition of the present invention. Preferably, the total concentration of the polymeric thickener system can be as little as about 0.5% by weight, based on the total weight of the composition. For certain embodiments, however, the total concentration of thickener system is greater than about 2% by weight, based on the total weight of the composition.

As used herein, a polymeric thickener is considered part of the thickener system if it is nonionic or cationic and its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than about 20,000) do not increase the viscosity of the composition significantly. These are considered an emollient or humectant, for example, rather than part of the thickener system.

The cationic polymers of this invention are selected from both permanently charged quaternary polymers (those polymers comprising quaternary amines such Polyquaternium 4, 10, 24, 32, and 37 described below) as well as protonated primary, secondary and tertiary amine functional polymers which have been protonated with a suitable protonic acid. Preferred protonated cationic polymers are based on tertiary amines. The protonated cationic polymers are preferably protonated with suitable acids that will not result in undue skin irritation such as C1-C10 alkylcarboxylic acids optionally substituted by oxygen (e.g., acetic acid, alpha hydroxyacids such as lactic acid, gluconic acid, and the like), C1-C10 alkylsulfonic acids (e.g., methylsulfonic acid and ethylsulfonic acid), C1-C10 alkylhydrogensulfates (e.g., methylhydrogensulfate) and mineral acids (e.g., hydrochloric acid, hydrobromic acid, sulfuric acid, and phosphoric acid and the like). The charge on protonated cationic polymers is pH dependent. For this reason, in order to ensure the polymer is sufficiently protonated, the pH must be adjusted appropriately and should be in the range of 5-9.5, preferably 6-8, and most preferably 6.5-7.5. It should be noted that it is not necessary to have all of the amines on a particular polymer protonated. The level of protonation will to a certain extent be pH dependent. With certain polymers in order to obtain optimum thickening with low skin irritation it may be beneficial to only protonate a small percentage of the available amine groups while with other polymers it may be beneficial to protonate substantially all of the amine groups. This will be easily determined by one skilled in the art. The quaternary, tertiary, secondary and primary amine functional polymers may be chosen from natural polymers, modified natural polymers as well as synthetic polymers. These polymers may be soluble or swellable in the hydroalcoholic solvent. Furthermore, these polymers may also possess hydrophobic side chains and thus be associative polymers.

In the compositions of the present invention, at least one of the polymeric thickeners in a pure state is a solid at ambient temperature. In preferred embodiments, all of the polymeric thickeners are solid at ambient temperature. Such solid polymers typically are those having a relatively high glass transition temperature (Tg). Preferably, solid polymers have a Tg of at least about 25° C., more preferably at least about 50° C., and most preferably at least about 80° C. Preferably, the solid polymeric thickeners are selected such that the composition has a viscosity of at least about 4,000 centipoise at 23° C.

Preferred thickener systems used in the compositions of the present invention are capable of producing viscoelastic compositions that are very stable. By varying the amount and type of polymer, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an elastic composition usually does not provide a cosmetically appealing product.

The thickener system includes at least one cationic or nonionic polymer that is solid at ambient temperature. A preferred group of cationic polymeric thickeners include cationically modified celluloses, quaternized natural aminofunctional polymers, and polymers based on ethylenically unsaturated monomers selected from the group of acrylates, acrylamides, vinyl lactams, vinyl acetates, methyl vinyl ethers, styrene, and acrylonitrile. A preferred group of nonionic polymeric thickeners include modified celluloses, associative polymers based on nonionic ethylenically unsaturated monomers wherein at least one comonomer has at least 16 carbon atoms, and polymers based on ethylenically unsaturated monomers selected from the group of acrylates, acrylamides, vinyl lactams, vinyl acetate and its hydrolyzed derivatives, methyl vinyl ethers, styrene, and acrylonitrile.

Such polymers can be classified as soluble, swellable, or associative in the hydroalcoholic solvent system. Some polymers may fall into one or more of these classes. For example, certain associative polymers can be soluble in the hydroalcoholic solvent system. Whether they are considered soluble, swellable, or associative in the hydroalcoholic solvent system, suitable polymers for use in the compositions of the present invention are those that are not capable of forming water-resistant films. Such polymers are not desirable because they would produce surgical hand preparations and antimicrobial hand lotions, for example, that could not be easily washed off with water after being applied and dried.

As used herein, a soluble polymer is one that in dilute solution (i.e. about 0.01-0.1% by weight in the desired hydroalcoholic solvent system), after heating for a sufficient time to ensure solubilization of any potentially soluble components, has no significant observable particles of greater than about 1 micron in particle size, as determined by light scattering measurements using, for example, Malvern Masterisizer E Laser Particle Size Analyzer available from Malvern Co., Boston, Mass.

As used herein, a swellable polymer is one that in dilute solution (i.e. about 0.01-0.1% by weight in the desired hydroalcoholic solvent system), after heating for a sufficient time to ensure solubilization of any potentially soluble components, has a significant (i.e., detectable) number of observable particles of greater than about 1 micron in particle size, as determined by light scattering measurements using, for example, Malvern Masterisizer E Laser Particle Size Analyzer.

As used herein, an associative polymer is one that has greater than 2 hydrophobic chains per polymer molecule of greater than about 16 carbon atoms.

Examples of such polymers are as follows.
Soluble Polymers—Cationic Natural Polymer Derivatives:

Cationic modified cellulosic polymers are reported in the literature to be soluble in water. Such polymers have been found to be useful in the present invention. When used at lower levels in combination with the appropriate emollients, no balling occurs as is often seen with neutral modified cellulose polymers. The most preferred modified cellulose products are sold under the trade names "CELQUAT" (National Starch and Chemicals Corp., Bridgewater, N.J.) and "UCARE" (Amerchol Corporation, Edison, N.J.). "CELQUAT" is a copolymer of a polyethoxylated cellulose and dimethyldiallyl ammonium chloride and has the Cosmetic, Toiletry and Fragrance Association (CTFA) designation Polyquaternium-4. The most preferred "CELQUAT" polymers are "CELQUAT" SC-230M and H-100. "UCARE" is a polymeric quaternary ammonium salt of hydroxyethylcellulose and a trimethyl ammonium chloride substituted epoxide and has the CTFA designation Polyquaternium-10. The preferred "UCARE" polymers have a high degree of cationic substitution. The most preferred "UCARE" polymer is "UCARE" JR-30M.

An alkyl modified quaternary ammonium salt of hydroxyethyl cellulose and a trimethyl ammonium chloride substituted epoxide has also been found to be useful. The polymer conforms to the CTFA designation Polyquaternium 24 and is commercially available as "QUATRISOFT" LM-200 from Amerchol Corp., Edison, N.J.

Soluble Polymers—Cationic Synthetic Polymers:

Synthetic cationic linear polymers useful in the present invention are preferably quite high in cationic charge density—generally having greater than 10% by weight cationic monomer, preferably greater than 25% by weight, and more preferably greater than 50% by weight. This ensures a good cosmetic feel and may actually improve hydroalcoholic solubility. In general, the polymers useful in the present invention have sufficient molecular weight to achieve thickening at generally less than about 5% by weight polymer but not too high that the lotion/cream feels slimy and stringy. While the composition of the polymer will dramatically affect the molecular weight at which sufficient thickening will occur, the polymers generally have a molecular weight of about 250,000 daltons to about 3,000,000 daltons, more preferably about 500,000 daltons to about 1,000,000 daltons. The homopolymers are comprised of one of the following monomers: methacryloyloxyalkyl trialkyl ammonium salt, acryloyloxyalkyl trialkyl ammonium salt, and quaternized dialkylaminoalkylacrylamidine salt. Preferably the polymers are copolymers comprised of at least two monomers selected from the group: trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, and acrylonitrile. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomers, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available as "Hypan QT-100" from Lipo Chemicals Inc., Paterson, N.J. It is quite effective at thickening hydroalcoholic systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance.

Soluble Polymers—Nonionic

A variety of cellulosic ethers are reported in the literature to be soluble in water. Such polymers have demonstrated the ability to viscosity hydroalcoholic solvent systems containing greater than about a 50:50 ratio of alcohol to water. Materials in this class that are nonionic and have been shown to be useful include: methylhydroxypropylcellulose, available as "BENECEL MP 943" from Aqualon, Wilmington, Del.; hydroxypropylcellulose, available as "KLUCEL" (LF, GF, MF, HF) from Aqualon, Wilmington, Del.; and hydroxybutylmethylcellulose (3.5% hydroxybutyl and 30% methoxyl) from Scientific Polymer Products, Ontario, N.Y.

Swellable Polymers

Many swellable polymers, which are slightly crosslinked, function as viscosifiers in hydroalcoholic solvent systems. In general, these swellable polymers are preferred because they tend to be far less "slimy" going on and once the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than about 1000 ppm, and preferably less than 500 ppm, based on the weight of the dry polymer.

A class of crosslinked polymers suitable for use in this invention are comprised of acrylamide and at least one other quaternary monomer selected from the group of trialkylaminoalkylacrylate and methacrylate salts, dialkyldiallyl ammonium salts, acrylamidoalkyltrialkyl ammonium salts, methacrylamidoalkyltrialkyl ammonium salts, and monomers comprising imidazolinium salts. The counterions are preferably $F^-$, $Cl^-$, $Br^-$, and $CH_3(CH_2)_nSO_4^-$ where n=0-4. Other comonomers may also be added including N-vinyl pyrrolidone, N-vinyl caprolactam, methyl vinyl ether, acrylates, methacrylates, styrene, and the like. A particularly preferred polymer is comprised of a poly(2-methacryloxyethyl trimethyl ammonium chloride) polydimethylaminoethyl methacrylate, which conforms to the CTFA designation Polyquaternium 37. Another preferred polymer is comprised of acrylamide and methacryloyloxyethyl trimethyl ammonium chloride, which conforms to the CTFA designation Polyquaternium 32. These are commercially available from Allied Colloids Inc. of Suffolk, Va. as "SALCARE" SC95, SC96, and SC92.

Other swellable polymers (i.e., slightly crosslinked polymers) can be prepared using ionizing radiation to crosslink. For examples, polymers comprising N-vinyl lactams, such as N-vinyl pyrrolidone, when exposed to gamma radiation increase in molecular weight and may actually crosslink. This crosslinking allows for more efficient thickening (less polymer required to achieve a certain viscosity) and an improved cosmetic feel. Other polymers that when exposed to gamma radiation result in crosslinking, include polymers such as "LUVIQUAT HM 552" (copolymers of vinylimidazolium methochloride and vinylpyrrolidone, which conforms to the CTFA designation Polyquaternium-16), and "GAFQUAT HS-100" (vinylpyrrolidone/methacrylamidopropyltrimethylammonium chloride copolymer which conforms to the CTFA designation Polyquaternium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups as used herein include substituted derivatives. Exemplary compounds include divinyl, diallyl, or dimethallyl esters, ethers, amides, or ureas. Specific examples are disclosed in U.S. Pat. Nos. 5,225,473 (Duan) and 4, 931, 282 (Asmus et al.).

A range of crosslinked polyvinylpyrrolidone (PVP) materials have been prepared via covalent crosslinking with diallyl maleate or by radiation crosslinking of linear PVP powders. Crosslinked PVP prepared under these techniques can produce colloidal particles which are highly swellable in hydroalcoholic solutions and thereby produce viscous solutions. The polymers are also nonionic and have excellent compatibility with chlorhexidine digluconate.

Associative Polymers

Associative polymers can be used in the thickening system of the compositions of the present invention. Such polymers thicken as a result of hydrophobic or Van de Waals association of hydrophobic side chains. Such associative polymers can form viscous to gelled hydroalcoholic solutions despite their relatively low molecular weights. Polymers that are alcoholic soluble can be modified by the addition of a long chain hydrophobic group. A preferred class of such associative polymers are based on nonionic ethylenically unsaturated monomers wherein at least one comonomer has at least 16 carbon atoms.

An example is cetyl hydroxyethylcellulose, available as "NATROSOL PLUS" from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. In hydroalcoholic systems of the present invention, the interpolymer associations can greatly improved if longer chain hydrophobic groups were used in place of the cetyl groups, since the C16 groups are not as insoluble as longer chain alkyls. For example, alkyl chains containing 18-31 carbon atoms, preferably 20-34 carbon atoms, provide particularly desirable polymeric thickeners in a hydroalcoholic solvent system containing at least about a 65:35 alcohol to water ratio. Long chain alkenyl and aralkyl groups may also be suitable.

Purity of Polymeric Thickeners

Attention may need to be paid to the purity of the thickener systems. For example, certain highly charged polymeric thickeners of the present invention are detrimentally effected by incorporation of ionic materials such as salts. Even low level ionic contaminants can significantly lower the viscosity. For this reason, many commercially available polymers are preferably cleaned prior to use such that there are substantially no excess ions for optimum performance. As used herein, "excess ions" refers to ions (other than the cations and counterions present in cationic polymers) that can be removed from the polymer by repeatedly washing with solvent.

Quaternary thickeners are particularly sensitive to excess ions in solution. For example, in embodiments where the secondary antimicrobial agent is a charged molecule such as a chlorhexidine salt (e.g., chlorhexidine digluconate), the excess ions reduce the viscosification efficiency of the quaternary thickener such that at a concentration of at least about 0.5% by weight chlorhexidine digluconate it is very difficult to formulate highly viscous systems above 60% lower alcohol. Commercial quaternary thickeners such as "SALCARE SC95" (referred to herein also as DMAEMA Q) have been found to have excess ions that prohibit their ability to thicken a 75% ethanol solution. By removing these excess ions, such as by repeated precipitations, for example, the excess salts and the polymer can effectively thicken even 75% alcohol solutions. Thus, for example, by removing excess ions, compositions containing a chlorhexidine salt in at least about 0.5% by weight, based on the total weight of the composition, can be thickened with a cationic polymeric thickener to a viscosity of greater than about 60,000 cps at 23° C.

The excess ions in solution can be monitored by evaluating cleaned and uncleaned polymer in 35% ethanol solutions with an ionic conductivity meter. The difference in the ionic conductivity of the cleaned verses uncleaned polymer is due to excess ions. It is desired that the ionic conductivity contribution of excess ions in the polymeric thickener, as measured using a Model 76 Conductivity Meter by Engineered Systems & Designs, Newark, Del., be less than about 50% of the ionic contribution of the polymer, preferably less than about 35%, more preferably less than 15%, and most preferably less than 5%, as determined in a desired hydroalcoholic solvent system (without any other additives). Generally, this is done in 35% ethanol/65% water, however, if the polymer is insoluble in this solvent system, it is carried out in 100% water. In either situation, the polymer should be conditioned in the solvent for 24 hours at 60° C. to extract the ions prior to conductivity testing. For the DMAEMA Q system, it is desired that the ionic conductivity in 35% ethanol, at 2.5% polymer loading be below 1,200 μmho, and preferably be below 1,000 μmho, and more preferably be below 900 μmho and most preferably be below 800 μmho.

Antimicrobials

In addition to the lower alcohols present in the composition of the present invention, other antimicrobials may be added to enhance the antimicrobial action of the compositions of the present invention. Such antimicrobials are referred to herein as "secondary antimicrobials." This may be particularly desirable in critical uses such as presurgical hand scrubs or presurgical patient skin scrub replacements. Suitable additional antimicrobials include iodine and its complexed forms such as povidone/iodine, chlorhexidine salts such as chlorhexidine digluconate (CHG), parachlorometaxylenol (PCMX), hexachlorophene, phenols, surfactants comprising a long chain hydrophobe (C12-C22) and a quaternary group, triclosan, "LAURICIDIN" glyceryl monolaurate, quaternary silanes, hydrogen peroxide, phenols, silver, silver salts such as silver chloride, silver oxide and silver sulfadiazine and the like. In order to reduce chances for irritation and yet maintain efficacy, the antimicrobial level should be adjusted to the minimum level which maintains a low bacteriological count for 6 and most preferably for 12 hours after application.

The most preferred secondary antimicrobial is chlorhexidine since it is capable of ensuring long term antimicrobial efficacy. If chlorhexidine is added to the present invention it is preferably present as a soluble salt. The diacetate and digluconate salts are preferred. The most preferred antimicrobial is chlorhexidine digluconate (CHG). CHG is preferably present at a concentration of about 0.05-5.0%, more preferably about 0.1-3%, even more preferably about 0.25-2%, and most preferably about 0.5-1%, by weight, based on the total weight of the composition. Chlorhexidine is a bis(diguanide) and therefore is very basic and is capable of forming multiple ionic bonds with anionic materials.

Optional Ingredients

In addition to alcohol, water, thickener system, and antimicrobial agents, the compositions of the present invention may optionally include ingredients such as pH buffers, emollients, antioxidants, fragrances, pharmaceutical agents, and propellants. It may also be beneficial to incorporate certain emulsifiers into the compositions of the present invention to ensure long-term stability of systems incorporating hydrophobic emollients.

Emollients

Emollients are typically added to hand lotions or hand preps because they act to increase the moisture content of the stratum corneum. Emollients are generally separated into two broad classes based on their function. The first class of emollients are lipophilic which function by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

For the purposes of this invention the emulsifier system is considered separate and distinct from any emollients which may be added even though it is recognized that the emulsifiers may function as occlusive emollients and aid in maintaining or improving the skin condition. Emollients are included in a preferred embodiment of the invention and preferably comprise between about 1% and about 30%, more preferably between about 2% and about 20% and most preferably between about 3% and about 12% by weight of the formulation.

Emollients may be selected from any of the classes known in the art. A general list of useful emollients appears in U.S. Pat. No. 4,478,853 and EPO patent application 0 522 624 A1 and in the *CTFA Cosmetic Ingredient Handbook* published by The Cosmetic, Toiletry, and Fragrance Association, Wash. D.C. (1992) under the listings "Skin Conditioning agents," "emollients," "humectants," "miscellaneous" and "occlusive," each of these references is hereby incorporated by reference. Preferred compositions of the present invention include both wax and liquid emollients.

In preferred embodiments, emollients are chosen from the following nonlimiting list of general emollients, occlusive lipophilic emollients and humectants. Examples of general emollients include short chain alkyl or aryl esters (C1-C6) of long chain straight or branched chain alkyl or alkenyl alcohols or acids (C8-C36) and their polyethoxylated derivatives; short chain alkyl or aryl esters (C1-C6) of C4-C12 diacids or diols optionally substituted in available positions by —OH; alkyl or aryl C1-C9 esters of glycerol, pentaerythritol, ethylene glycol, propylene glycol, as well as polyethoxylated derivatives of these and polyethylene glycol; C12-C22 alkyl esters or ethers of polypropylene glycol; C12-C22 alkyl esters or ethers of polypropylene glycol/polyethylene glycol copolymer; and polyether polysiloxane copolymers. In addition to many of the emulsifiers of preferred emulsifier systems, additional examples of occlusive emollients include cyclic dimethicones, polydialkylsiloxanes, polyaryl/alkylsiloxanes, long chain (C8-C36) alkyl and alkenyl esters of long straight or branched chain alkyl or alkenyl alcohols or acids; long chain (C8-C36) alkyl and alkenyl amides of long straight or branched chain (C8-C36) alkyl or alkenyl amines or acids; hydrocarbons including straight and branched chain alkanes and alkenes such as squalene, squalane, and mineral oil; polysiloxane polyalkylene copolymers, dialkoxy dimethyl polysiloxanes, short chain alkyl or aryl esters (C1-C6) of C12-C22 diacids or diols optionally substituted in available positions by OH; and C12-C22 alkyl and alkenyl alcohols. Nonlimiting examples of preferred humectant type emollients include glycerol, propylene glycol, dipropylene glycol, polypropylene glycol, polyethylene glycol, sorbitol, pantothenol, gluconic acid salts and the like.

Although the thickener system is responsible for the stability and overall consistency of compositions of the present invention, emollients may also affect the viscosity and stability of a composition. It is anticipated that a single emollient may be added to the present invention or two or more emollients may be added to the composition. A wide range of emollients may be added to the formulations of the present invention. Preferably wax and oil type emollients along with water soluble emollients are used. In a preferred embodiment, emollient systems are comprised of humectants in addition to occlusive wax and oil emollients in concentrations which achieve a moisturizing but not greasy composition which maintains and improves the condition of the skin upon repeated use. Ideally, emollients are non-comedogenic and are chosen to ensure no skin irritation or sensitization reaction occurs. This is particularly critical since the composition of the present invention will likely be worn in an occluded condition under surgical gloves. Furthermore, emollients should be chosen which do not affect the integrity of the glove material. For example, since hydrocarbon emollients such as mineral oil and petrolatum can detrimentally affect the tear strength of surgical gloves, these emollients may need to be avoided for compositions employed as presurgical disinfectants.

Certain emollients which are insoluble in the hydroalcoholic solvent can be emulsified in what is believed to be a separate and distinct emulsion. These emollients have little affect on the melt temperature of a composition. For example, certain cyclic silicones, polysiloxanes, and dialkoxypolysiloxanes can be emulsified in hydroalcoholic solvents using polyether/polysiloxane copolymers surfactants.

The following are nonlimiting examples of emulsifier/emollient components which improve thickening/stability of compositions of the present invention.

a. Certain wax emulsifiers/emollients have been found to be particularly useful and include solid waxy esters such as: myristyl myristate, cetyl palmitate, myristyl stearate, stearyl behenate, behenyl isostearate, isostearyl behenate, behenyl behenate, lauryl behenate, behenyl erucate. These have the following formula: $R^{12}$—$CO_2$—$R^{13}$ wherein $R^{12}$ is an alkyl or alkenyl group of at least 14 carbon atoms, and $R^{13}$ is an alkyl or alkenyl group of at least 4 carbon atoms.

b. Long chain hydrocarbon di-esters or tri-esters of polyhydric alcohols with a melting point of greater than 23° C., including solid esters such as glycerol tribehenate and sorbitan tristearate.

c. Pure lanolins and lanolin derivatives (e.g., hydrogenated lanolin), which provide excellent emolliency but can also improve the stability of the emulsion when used in combination with oil emollients.

d. Petrolatums, which are mixtures of oily and waxy long chain hydrocarbons, provide excellent emolliency, and can also improve the stability of the emulsion when used in combination with oil emollients.

e. Microcrystalline waxes and branched hydrocarbon waxes with a melting point of greater than 50° C. and a molecular weight of greater than 400. Examples of this includes, but is not limited to, "VYBAR 103" branched hydrocarbon with a number average molecular weight of 2800, and "ULTRAFLEX" microcrystalline wax, both of which are available from Petrolite Corp. of Tulsa, Okla.

f. Oxidized waxes and modified hydrocarbon waxes, which are prepared from waxes modified by oxidation, salts of oxidized waxes, maleic anhydride adducts of polyolefins and urethane derivatives of oxidized synthetic or petroleum waxes. Applicable waxes could include Petrolite's Cardis or Petronauba microcrystalline and polyethylene-based oxidized products, Polymekon (salts) and Ceramer (anhydride adducts).

g. Fully saturated homopolymers of polyethylene, or copolymers of various alkene monomers having a molecular weight at or below 3,000 with a melting point below 130° C. and low melt viscosities. Applicable waxes could include "POLYWAX" available from Petrolite Corp.

Fragrances

The compositions of the present invention may also comprise a fragrance. If fragrances are included the fragrances must be chosen carefully since some fragrances are known to cause skin irritation and/or sensitization reactions.

Propellants

The compositions of the present invention may also be formulated into an aerosol foam or mousse by addition of an appropriate propellant. The propellant must be chosen to ensure proper delivery from the container to prevent clogging of the valve. The propellant can be chosen from chlorofluorocarbons (CFCs), hydrochlorofluorocarbons (HCFCs), hydrofluorocarbons (HFCs), perfluorinated alkanes, and lower alkanes (C1-C5) as well as nitrous oxide dimethyl ether and other solvent-soluble propellants. Preferred propellants are lower alkanes such as propane, butane, and isobutane since these result in a dramatic loss in viscosity making the formulation easy to dispense. A 70:30 mixture of propane/isobutane is a particularly preferred embodiment. In order to produce an aerosol composition the antimicrobial lotion is first formulated and charged into an appropriate pressure rated container. If convenient, the formulation may be heated above the melt temperature in order to facilitate filling. The propellant is then added under pressure at approximately 2-30% preferably 3-20% by volume. The propellant may form a separate layer or may remain emulsified in the composition.

Pharmaceutical Agents

Pharmaceutical agents (e.g., medicaments, drugs, prodrugs, etc.) suitable for use in compositions of the present invention are compounds that are intended to be delivered transdermally (i.e., into the skin and/or through the skin into the circulatory system) to a mammal to alter biological function to treat, cure, and/or prevent disease or abnormal conditions.

Suitable pharmaceutical agents exhibit an optimal combination of such properties as water solubility, polarity, structure, and molecular weight. For instance, molecular weights are typically between about 100 daltons and about 5000 daltons, and preferably between about 200 daltons and about 1200 daltons. Examples of suitable pharmaceutical agents include those described in U.S. Pat. No. 4,752,612 (Saito et al.).

Suitable pharmaceutical agents include antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g. nystatin); vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219) antiulceratives such as H2 antagonists; steroidal hormones (e.g., progesterone, testosterone, estradiol, levonorgesterel); antivirals and/or immunomodulators (e.g., 1-isobutyl-1H-imidazo[4,5-c]quinolin-4amine, 1-(2-hydroxyl-2-methylpropyl)-1H-imidazo[4,5-c]quinoline-4-amine, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones LHRH); cardioactive products such as atriopeptides; proteinaceous products (e.g., insulin); enzymes (e.g., anti-plague enzymes, lysozyme, dextranase), antinauseants (e.g., scopolamine); anticonvulsants (e.g., carbamazepine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatriptan); antiarrhythmic agents (e.g., flecamide); antiemetics (e.g., metoclopramide, ondansetron); anticancer agents (e.g., methotrexate); neurologic agents such as anxiolytic drugs; hemostatics; antiobesity agents; nicotine; and the like, as well as pharmaceutically acceptable salts and esters thereof.

The pharmaceutical agent is present in a transdermal delivery device of the invention in a therapeutically effective amount, i.e., an amount effective to bring about a desired therapeutic result in the treatment of a condition. The amount that constitutes a therapeutically effective amount varies according to the particular pharmaceutical agent incorporated in the device, the condition being treated, any pharmaceutical agent being coadministered with the selected pharmaceutical agent desired duration of treatment, the surface area of the skin over which the device is to be placed, the type of device being utilized, the choice of excipients, and other components of the device.

Penetration Enhancers

Additional compounds other than the lower alcohol or components of the emulsifier system may also be present in the composition to further boost the penetration of a particular pharmaceutical agent. These penetration enhancers may be present primarily in either the oil-like phase of the emulsion or the hydroalcoholic phase. Non-limiting examples of additional penetration enhancers include $C_8$-$C_{22}$ fatty acids such as isostearic acid, octanoic acid, and oleic acid; $C_8$-$C_{22}$ fatty alcohols such as oleyl alcohol and lauryl alcohol; lower alkyl esters of $C_8$-$C_{22}$ fatty acids such as ethyl oleate, isopropyl myristate, butyl stearate, and methyl laurate; di (lower) alkyl esters of $C_6$-$C_8$ diacids such as diisopropyl adipate; monoglycerides of $C_8$-$C_{22}$ fatty acids such as glyceryl monolaurate; tetrahydrofurfuryl alcohol polyethylene glycol ether; polyethylene glycol, propylene glycol; 2-(2-ethoxyethoxy) ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Certain emulsifier systems may also significantly increase the flux of particular pharmaceutical agents. This may be particularly true of emulsifiers that are in a pure state liquids at skin temperature such as those having shorter chain hydrophobes (e.g., methyl laurate), unsaturated hydrophobes (methyl oleate, oleic acid, oleyl alcohol, glycerol monooleate), and branched hydrophobic hydrocarbon chains (isostearyl alcohol).

Transdermal Delivery Systems

The compositions of the present invention can be used in a variety of transdermal delivery systems (e.g., devices). A variety of such systems have been described. The simplest is a lotion of a pharmaceutical agent in the composition of the present invention. Others include matrix devices in which a pharmaceutical agent is incorporated into the composition of the present invention and placed within a polymeric material such as a hydrogel layer or adhesive; reservoir devices in which the pharmaceutical agent-containing hydroalcoholic composition is delivered to the skin through a rate-controlling membrane; drug-in-adhesive devices in which the pharmaceutical agent is placed within the composition of the present invention as part of an adhesive composition; and more complex multilaminate devices involving several distinct layers (e.g., layers for containing the pharmaceutical agent, for containing excipients, for controlling the rate of release of the pharmaceutical agent and excipients, and for attaching the device to the skin). Each of these devices include an adhesive to maintain contact with the patient's skin and a backing that protects the device from external factors while in use, thereby forming a patch.

An exemplary reservoir device comprises a backing, a matrix containing the composition of the present invention with the pharmaceutical agent therein, optionally a membrane for controlling the rate at which the pharmaceutical agent is delivered to the skin, an adhesive layer, and a release liner.

Alternative Applications for the Compositions

The compositions of this invention may be compounded with UV absorbers and oils to deliver fast-drying sunscreens. Antimicrobials such as benzoyl peroxide may also be added to the formulations and the formulations may be useful as an acne medication. The systems of this invention may also be formulated with barrier compounds to form barrier creams and lotions. Materials which may be added to provide barrier protection for use as skin barriers to protect against diaper rash include but are not limited to 0.1 to 60% aldioxa, allantoin, aluminum acetate, aluminum hydroxide, bismuth subnitrate, boric acid, calamine, cellulose (microporous), cholecalciferol, cocoa butter, cod liver oil (in combination), colloidal oatmeal, cysteine hydrochloride, dexpanthenol, dimethicone, glycerin kaolin, lanolin (in combination), live yeast cell derivative, mineral oil, Peruvian balsam, Peruvian balsam oil, petrolatum, protein hydrolysate (1-leucine, 1-isoleucine, 1-methionine, 1-phenylalanine, and 1-tyrosine), racemethionine, shark liver oil, sodium bicarbonate, sulfur, talc, tannic acid, topical starch, vitamin A, white petrolatum, zinc acetate, zinc carbonate and zinc oxide. Formulations are also contemplated containing antifungal agents for treating fungal infections of the skin such as athlete's foot and the like. The compositions of the present invention can be dispensed in a discreet, substantially uniform amount using the dispensers disclosed in Applicants' Assignees' Copending U.S. patent application Ser. Nos. 08/668,198, filed Jun. 21, 1996, entitled "Dispenser for Antimicrobial Liquids" and 08/668,270, filed Jun. 21, 1996 entitled "Drip Resistant Nozzle for a Dispenser".

Methods of Preparation

The compositions of the present invention may be prepared by a variety of techniques. For example, the process can often be as simple as adding the polymer to the hydroalcoholic solvent at a temperature above the melting point of any solid emulsifiers, mixing briefly and cooling. For compositions containing insoluble emollients and/or emulsifiers, it may be beneficial to mix the components under high shear (e.g., using a homogenizer).

In general it works well to melt any solid components such as emulsifiers with aqueous-insoluble emollients together in one vessel and add these to the hydroalcoholic solvent and any aqueous miscible emollients along with the polymeric thickening agent. It may be beneficial to heat the system. The processing variables including amount and intensity of high shear mixing, rate of cooling, and order of addition are easily determined by one skilled in the art.

Test Methods

Viscosity

In the following Examples (except where indicated) viscosity was measured at 23° C. at ambient pressure using a Brookfield LVDV-I+ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20-80% of the viscometer range and more preferably between 30-70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines preferred spindles for various sample viscosities.

| Sample Viscosity | T Spindle to Use |
|---|---|
| 1,000-100,000 | B |
| 10,000-200,000 | C |
| 50,000-500,000 | D |
| 100,000-1,250,000 | E |
| 500,000-3,000,000 | F |

The viscosity of each sample was taken as the highest relatively stable reading achieved on the first path the spindle traversed using the heliopath adapter.

Stability

The stability of samples was measured 24 hours after conditioning at ambient conditions by placing 12 ml of a formulation that formed a lotion/cream in a 15 ml graduated centrifuge tube. The tube was then centrifuged in a Labofuge B (Heraeus Sepatech GmbH, Model 2650, rotor 2150 and buckets #2101) at 2000 rpm (1545×g when measured at the longitudinal midpoint of the sample tube) for 30 minutes at 23° C. Stability is recorded as a volume percent separation in the Examples below.

Minimum Inhibitory Concentration (MIC)

An overnight culture of *E. coli* ATCC8739 (lab strain 223) and/or *S. Aureus* ATCC14154 (lab strain 502) grown on trypticase soy agar plates was resuspended in Mueller-Hinton Broth to a cell density of 0.6-1.2×10$^6$ colony forming units per milliliter. Chlorhexidine samples were prepared by adjusting CHG to 512 μg/ml in Mueller-Hinton Broth and serially diluting in two-fold steps in Mueller-Hinton Broth. The CHG-containing Mueller-Hinton Broth was placed in 96-well sterile microliter plates and each well was inoculated with the bacteria. The plates were then incubated for 24-48 hours at 37° C. Bacterial growth was determined visually by comparing the plates. The MIC was determined as the lowest concentration of CHG that resulted in complete kill of the test organism.

EXAMPLES

The following Examples are provided to illustrate the invention and are not intended to limit the scope of the invention.

Example 1

Quaternary Cellulose Thickeners and Viscosity

A series of antimicrobial compositions was prepared using the following base formula:

| Component | Wt. % |
|---|---|
| Lanette 14 (Myristyl alcohol)[1] | 0.5 |
| Arlamol E (PPG-15 stearyl ether)[2] | 0.5 |
| Ethanol/Water (65:35 by wt) | 99.0 |

[1]Witco, Humko Chemical Div., Memphis, Tenn.
[2]ICI Surfactants, Wilmington, Delaware To this base emollient/solvent system was added "CELQUAT" polymer and chlorhexidine digluconate (CHG) in the amounts shown in the table below. The polymer was added as a powder, shaken vigorously and placed in a 60° C. oven overnight to ensure complete dissolution. The CHG was added as a 20% (weight by volume) solution in water in the amount necessary to reach the final concentration indicated.

| Polymer | Concentration (Wt %) | Conc. CHG (Wt. %) | Viscosity* (cps) |
|---|---|---|---|
| CELQUAT 230M | 1.0 | 0 | 1600 |
| | 1.0 | 0.5 | 1600 |
| | 1.0 | 1.0 | 1600 |
| | 2.0 | 0 | 31000 |
| | 2.0 | 0.5 | 34000 |
| | 2.0 | 1.0 | 33000 |
| CELQUAT H-100 | 2.0 | 0 | 2000 |
| | 2.0 | 0.5 | 2000 |
| | 2.0 | 1.0 | 1800 |
| | 3.0 | 0 | 8800 |
| | 3.0 | 0.5 | 9400 |
| | 3.0 | 1.0 | 7700 |

*Brookfield Viscosity using a Brookfield LVT viscometer with spindle #3.

The results indicate that both "CELQUAT" polymers are capable of thickening a hydroalcoholic solvent system. Also, the viscosity is not significantly affected by the presence of CHG. The results also indicate that "CELQUAT 230M" is a much more effective thickener, achieving significantly higher viscosity at 2% by weight than the "CELQUAT H-100" at 3% by weight. The higher viscosity at lower solids content generally results in better cosmetic properties.

Example 2

Quaternary Cellulose Thickeners and Effect of Solvent and Emollient System

The following formulations were made in a similar fashion as that described in Example 1 except that both the CHG and silicone detackifier (if present) were added after heating.

| Formula | A | B | C | D | E | F | G |
|---|---|---|---|---|---|---|---|
| 200 Proof Ethanol | 61.1 | 68.8 | 61.3 | 61.0 | 63.1 | 63.1 | 61.4 |
| Distilled Water | 30.4 | 24.7 | 33.0 | 33.3 | 29.5 | 29.5 | 30.6 |
| 20% CHG | 5.0 | 5.0 | 5.0 | 5.0 | 5.0 | 5.0 | 5.0 |
| Arlamole E | 0.75 | 0.75 | 0.75 | 0.75 | 0.75 | 0.75 | 0.75 |
| Lanette 14 | 0.75 | 0.75 | | | 0.75 | 0.75 | 0.75 |
| Celquat 230 M | 2.0 | 2.0 | 2.0 | 2.0 | 2.0 | 2.0 | 2.0 |
| Ucare JR-30 M | | | | | | | 1.0 |
| Ceraphyl 424[1] | | | 0.75 | 1.0 | | | |
| Abil EM-90[2] | | | | | 0.94 | | |
| 200 Fluid, 200 ctks[3] | | | | | | 0.75 | 0.75 |

[1]Myristyl Myristate available from ISP Van Dyk Inc. Belleville, NJ
[2]Cetyl dimethicone copolyol; Goldschmidt Chemical Corp., Hopewell VA.
[3]Polydimethylsiloxane available from Dow Corning Corp., Midland MI The viscosity of Samples A and B were measured on a Brookfield LVT viscometer using spindle #3 with the following results:

| Sample | Spindle Speed (RPM) | Viscosity (cps) |
|---|---|---|
| A | 1.5 | 45600 |
| | 3.0 | 34200 |
| B | 1.5 | 46800 |
| | 3.0 | 36800 |

These results indicate that the viscosity is not dependent on the level of ethanol within the range 64:36 to 71:29 ethanol: water. The shear rate appears to influence the viscosity since at higher viscometer rotational speeds the viscosity is reduced.

Samples A and B had a somewhat slimy feel during application and became tacky as the lotion dried and even after drying. Samples C and D also had a somewhat slimy feel during application but sample C was only slightly tacky as the lotion dried and after drying. Sample D was non-tacky once dried. Samples E and F were significantly less tacky and had a nice feel when dry. Sample G was somewhat slimy going on but had a nice feel when dry and did not ball.

Example 3

Quaternary Acrylates

The quaternary ethylenically unsaturated monomer containing polymers such as quaternary acrylates or quaternary acrylate copolymers are quite sensitive to ion concentration and can suffer dramatic viscosity losses upon addition of minor concentrations of salts. The graph shown in FIG. 1 illustrates the viscosity loss of:
  a. "SALCARE SC92," a copolymer of acrylamide and methacryloyloxyethyl trimethyl ammonium chloride having CTFA designation Polyquaternium 32.
  b. "SALCARE SC95," a homopolymer of methacryloyloxyethyl trimethyl ammonium chloride having CTFA designation Polyquaternium 37.

Both of these products are supplied as 50% polymer concentration in a mineral oil inverse emulsion. For each polymer 4 g of the polymer emulsion (2 grams of polymer) was added to 96 grams of warm (60° C.) 68:32 ethanol water and shaken vigorously. The mixture was allowed to sit overnight. CHG was added as a 20% aqueous solution in small aliquots and the viscosity was measured after each addition using a Brookfield DV-I+ with a model D heliopath and a T spindle. The viscosity is shown in FIG. 1.

FIG. 1 illustrates that as CHG is added the viscosity progressively drops. The viscosity of "SALCARE SC92" is greater than that of SC95 at each concentration. The viscosity achieved may be further increased by ensuring minimum incorporation of salts or salt contamination. For example, as received from the supplier, "SALCARE SC92" contains ionic contaminants. If these are removed by the procedure in Example 9, a higher viscosity composition results. This is shown below for 68:32 ethanol/water containing 0.5% CHG and 4% polymer.

| Polymer | Viscosity (cps)[1] |
|---|---|
| SALCARE SC92 (As received) | 15,000 |
| SALCARE SC92 (cleaned) | 84,000 |

[1]Measured using a Brookfield DV-I+ with a model D heliopath and a T spindle.

Example 4

Compostions Containing "SALCARE SC-92" Polymer

The following formulation was prepared using "SALCARE SC-92" as the thickener. The emollients were added to the ethanol/water solution and heated to 65 C. for 1 hour at which point all waxes were melted. The "SALCARE" was added and the contents shaken vigorously and then mixed well using a high shear rotor/stator mixer. The formulation was allowed to sit overnight prior to evaluation.

| Emollient Trade Name | Chemical Description | Wt. % |
|---|---|---|
| POLAWAX A31 | ceteareth-20, cetearyl alcohol | 1.5 |
| GANEX V220 | copolymer NVP/1-eicosene, MW = 8600 | 0.38 |
| CERAPHYL 28 | cetyl lactate | 0.74 |
| LANETTE 14 | myristyl alcohol | 0.74 |
| BERNEL Ester 2014 | arachidylmyristate | 0.56 |
| LIPOVOL MOS130 | dipentaerythrityl hexacaprylate/hexacaprate tridecyl stearate, tridecyltrimellitate | 0.56 |
| LEXOL PG865 | propylene glycol dicaprylate/dicaprate | 0.56 |
| SALCARE SC92 | Polyquaternium 32 (50% in mineral oil) | 2.4 |

This formulation had a thick rich feel during application. The lotion dried rapidly without tackiness and had a nice feel once dried.

Example 5

Compositions Containing "HYPAN OT-100" or "SALCARE SC-92"

The following formulations were prepared using "HYPAN QT-100" and "SALCARE SC-92" as the thickeners. The emollients were added to the ethanol/water solution and heated to 65° C. for 1 hour at which point all waxes were melted. The "HYPAN QT-100" polymer was gradually added while mixing at high speed with a high shear rotor/stator mixer. This was mixed until well blended. To sample C, the "SALCARE SC-92" was added, the contents shaken vigorously, and once again sheared with the high shear mixer.

| Emollient Trade Name | Wt % | | |
|---|---|---|---|
|  | A | B | C |
| POLAWAX A31 | 1.5 | 1.5 | 1.5 |
| GANEX V220 | 0.37 | 1 | 0.37 |
| CERAPHYL 28 | 0.74 | 0.74 | 0.74 |
| LANETTE 14 | 0.74 | 0.74 | 0.74 |
| BERNEL Ester 2014 | 0.56 | 0.56 | 0.56 |
| LIPOVOL MOS130 | 0.56 | 0.56 | 0.56 |
| LEXOL PG865 | 0.56 | 0.56 | 0.56 |
| HYPAN QT-100 | 1.0 | 1.0 | 0.75 |
| SALCARE SC92 |  |  | 0.5 |

Sample A had a jelly/custard like consistency with a fairly long dry time. After drying the product felt smooth. The "HYPAN" polymer gave the product an objectionable odor which quickly fades. This could probably be eliminated by proper clean up of the polymer. Sample B had a thicker richer consistency than A with a soft feel. Sample C had a nice consistency and was not jelly or custard-like. Sample C was smooth, non-tacky, and not greasy.

Example 6

Compositions Containing Linear Synthetic Quaternary Polymers

A series of linear quaternary polymers was acquired from Nalco Chemical Company, Naperville, Ill. and evaluated for use in hydroalcoholic systems. Each polymer was supplied as an inverse emulsion in a hydrocarbon oil (except for 2240 which was supplied as an aqueous solution.) The polymers were added to the hydroalcoholic solution at a concentration of 2% by weight. The following table summarizes the polymer properties:

| Trade Name | Composition | Polymer[2] MW | Soluble in 50% EtOH | Soluble in 68% EtOH | Comments |
|---|---|---|---|---|---|
| 7190 | acrylamide | >10 MM | Y | Y | elastic, stringy, modified cationic |
| 7130 | acrylamide | >5 MM | Y | Y | elastic, stringy, modified cationic |
| 7520 | acrylamide | >10 MM | Y | Y | elastic, stringy, modified cationic |
| 7585 | acrylic cationic | 2.5 MM | Y | Y | less elastic, better consistency |
| 2240 | polymethacrylamidopropyl trimethylammoniium chloride | 50–100 K | Y | Y | very low viscosity |
| 92LT175 | quaternized dimethylamino ethylacylate | 1 MM | Y | N | less elastic, good consistency[1] |

[1]Composition had a slimy feeling during application and during wash off. It was somewhat sticky during dry down.
[2]Reported Molecular Weight - MM indicates $10^6$ and K indicates $10^3$ units in daltons.

The data appears to indicate that linear synthetic polymers preferably have a molecular weight of less than 1 MM cps. Clearly those polymers with a molecular weight of >5 MM form a composition which is more elastic than desired. The data also indicates that the percent charge alone does not determine the solubility characteristics.

Example 7

Compositions Containing Gamma Exposed N-Vinyl Pyrrolidone Copolymers

Polyvinylpyrrolidone (PVP) can be crosslinked by exposure to gamma radiation. This can also be done using copolymers of NVP and at least one other monomer. For use in this invention the copolymer preferably includes a quaternary functionality. The two polymers used are described below:

| Trade Name | Composition | MW | Manufacturer |
|---|---|---|---|
| Luviquat HM552 | 50:50 copolymer of NVP and vinylimidazolium methochloride (CTFA Polyquaternium 16) | 800,000 | BASF |
| Gafquat HS-100 | copolymer of NVP and methacrylamidopropyl-trimethylammonium chloride (CTFA Polyquaternium 28) | — | ISP |

A portion of these polymers (which are supplied as 20% aqueous solutions) were dried down into films at room temperature. The films were broken up into approximately 0.5 square centimeters in pieces sealed in glass jars and passed through a cobalt gamma sterilization unit. The polymers were exposed two doses of radiation at 42.2-44.7 Mrad and 15 Mrad of radiation, which was an excessive level. After exposure to gamma radiation the dry polymer was ground to a fine powder using a Waring blender. The data in the table below shows the viscosities for compositions containing 2% by weight polymer. The polymer was added to the solvent (60:40 ethanol/water by weight) and heated to 70° C. for 2 hours and cooled overnight. Additional samples of the gamma irradiated "LUVIQUAT HM552" were sheared with a high shear mixer. Sample e was sheared after the polymer was heated and completely swollen. Samples b, c, f-j, l-m were sheared immediately after addition of the polymer to the ethanol/water solution followed by heating the mixture to 72° C. for 4 minutes. When cool, CHG was added to a concentration of 0.5% by weight to the samples indicated in the table below.

| Sample | Polymer | Gamma (Mrad) | Shear | [polymer] % | [CHG] % | Viscosity (cps) |
|---|---|---|---|---|---|---|
| a | Luviquat HM552 | 0 | none | 2 | 0 | 55 |
| b | Luviquat HM552 | 17 | none | 2 | 0 | 265 |
| c | Luviquat HMSS2 | 17 | none | 4 | 0 | 625 |
| d | Luviquat HM552 | 43 | none | 2 | 0 | 850–2200 |
| e | Luviquat HM552 | 43 | shear | 2 | 0 | 11,500 |
| f | Luviquat HM552 | 43 | shear | 2 | 0 | 8500 |
| g | Luviquat HM552 | 43 | shear | 2 | 0.5 | 870 |
| h | Luviquat HM552 | 43 | shear | 3 | 0.5 | 12,000 |
| i | Luviquat HM552 | 43 | shear | 4 | 0 | 60,000–80,000 |
| j | Luviquat HM552 | 43 | shear | 4 | 0.5 | 25,000–30,000 |
| k | Gafquat HS-100 | 0 | none | 2 | 0 | 204 |
| l | Gafquat HS-100 | 17 | shear | 2 | 0 | 3000 |
| m | Gafquat HS-100 | 17 | shear | 3 | 0 | 8400 |
| n | Gafquat HS-100 | 43 | shear | 2 | 0 | 160 |

This data indicates that for "LUVIQUAT HM552" (copolymer of NVP and vinylimidazolium methochloride) the level of gamma irradiation needs to be fairly high to ensure sufficient viscosity enhancement. It appears that for Gafquat HS-100 exposure to gamma irradiation at high levels (43 Mrad) may produce excessive crosslinking that results in a decreased viscosity. For the "GAFQUAT HS-100" polymer, 17 Mrad may also be excessive. This experiment has not determined the optimum exposure level.

Example 8

Associative Polymer

An associative polymer was prepared by reacting octadecylisocyanate (Mondur O, Bayer Pittsburgh, Pa.) with polyethylene imine (Polymin P SG, BASF Corp. Mount Olive N.J.) and further neutralizing a percentage of the residual amine groups. Specifically, to a solution of Polymin P SG in ethanol/water was added Mondur 0 through a 0.2 um syringe filter to remove any particulate. This was allowed to react at room temperature for 60 min. After this time concentrated HCl (37%) was used to neutralize a portion of the residual amino groups on the polyethyleneimine. In order to achieve a functional associative thickener, i.e. a polymer that will yield a stable composition having a viscosity in excess of 4000 cps, the proper level of hydrophobe substitution (reaction with Mondur O) and neutralization with HCl was necessary. The table below summarizes several formulations in terms of the level of reactants used. All weights are in grams.

| Polymin** (g) | Mondur O (g) | HCl (g) | EtOH/ water | solvent (g) | Viscosity (cps) |
|---|---|---|---|---|---|
| 30.0 | 20.6 | 1.72 | 44.4 | 270 | 2000 |
| 30.0 | 20.6 | pH 7.5* | 44.4 | 270 | 158000 |
| 30 | 15.4 | 1.72 | 44.4 | 270 | 245000 |
| 30 | 15.4 | 3.44 | 44.4 | 270 | <10, unstable |

*HCl was added until the pH was adjusted to 7.5
**Polymin SG is supplied as a 50% by weight solution in water.

Example 9

Quaternary Acrylate Polymer of Crosslinked Dimethylaminoethyl Methacrylate

A quaternary acrylate polymer composed of colloidal particles of lightly crosslinked dimethylaminoethyl methacrylate quaternized using methyl chloride, is available from Allied Colloids Inc. as Salcare SC95 and SC96. The base polymer, once cleaned by precipitation from the carrier oils and residuals, can be formulated to provide stable, viscous hydroalcoholic lotions. The cleaning procedure is desirable to ensure maximum viscosity enhancement as well as minimal odor.

The polymer was cleaned by placing 200 gm of Salcare SC95 into a glass container and adding 200 gms of toluene. The solution was mixed and then approximately 2500 gm of acetone was added with additional mixing. A high shear mixer was placed into the container to create a vortex. Slowly 125 gms of distilled water was added into the vortex. A white polymer precipitated. After agglomeration, the solvent phase was poured off. To the polymer dough was added 500 gm of distilled water, and 700 gms of acetone. Using the mixer a uniform solution was created. Again using the mixer to create a vortex 600 gms of acetone was added. The polymer again agglomerated, and the liquid phase was poured off. To the polymer dough was added 350 gms of distilled water and 700 gms of acetone. The mixer was wed to create a uniform solution. Again using the mixer to create a vortex 600 gms of acetone was added. The polymer agglomerated, and the liquid phase was poured off. The doughy polymer was placed in a polyethylene bag and squeezed to remove additional solvent. The resulting polymer dough was dried in a vacuum oven, overnight, at 30° C. and at maximum vacuum.

Fully swollen "SALCARE 95" (DMAEMA Q) colloidal particles in ethanol/water (68:32 weight ratio) have a particle size range from 1 to 25 microns. The mean particle size is 7 microns, as determined by a Malvern Mastersizer E, utilizing light scattering.

The following compositions were prepared using the cleaned "SALCARE SC95" (DMAEMA Q) according to the procedure above. The DMAEMA Q polymer was first placed in the alcohol and water solution and allowed to swell with occasional mixing. The emollients myristyl alcohol, dimethicone, PG 15 stearyl ether and CHG (if used) were then added to the viscous solution with mixing until uniform.

| | Formulas |
|---|---|
| | A (0% CHG) |
| 0.85 g | DMAEMA Q polymer |
| 0.25 g | Myristyl Alcohol, Lanette 14, Henkel |
| 0.25 g | Dimethicone, L45/350, Union Carbide |
| 0.25 g | PPG-15 Stearyl Ether, Arlamol E, ICI |
| 34.67 g | 190 Proof Ethanols |
| 13.78 g | Distilled Water |
| | B (0.25% CHG) |
| 1.30 g | DMAEMA Q polymer |
| 0.25 g | Myristyl Alcohol, Lanette 14, Henkel |
| 0.25 g | Dimethicone, L45/350, Union Carbide |
| 0.25 g | PPG-15 Stearyl Ether, Arlamol E, ICI |
| 0.65 g | Chlorhexidine Gluconate Solution, 20.48% wt/vol |
| 34.24 g | 190 Proof Ethanol |
| 13.06 g | Distilled Water |
| | C (0.50% CHG) |
| 1.75 g | DMAEMA Q polymer |
| 0.25 g | Myristyl Alcohol, Lanette 14, Henkel |
| 0.25 g | Dimethicone, L45/350, Union Carbide |
| 0.25 g | PPG-15 Stearyl Ether, Arlamol E, ICI |
| 1.30 g | Chlorhexidine Gluconate Solution, 20.48% wt/vol |
| 33.79 g | 190 Proof Ethanol |
| 12.41 g | Distilled Water |
| | D (1.00% CHG) |
| 1.75 g | DMAEMA Q polymer |
| 0.25 g | Myristyl Alcohol, Lanette 14, Henkel |
| 0.25 g | Dimethicone, L45/350, Union Carbide |
| 0.25 g | PPG-15 Stearyl Ether, Arlamol E, ICI |
| 2.60 g | Chlorhexidine Gluconate Solution, 20.48% wt/vol |
| 33.69 g | 190 Proof Ethanol |
| 11.26 g | Distilled Water |

Formulas A to C were gel-like lotions, formula D was a semi-viscous solution. High salt concentrations tend to reduce the viscosifying efficiency of DMAEMA Q at these high alcohol levels. Compositions A-C were essentially gelled, translucent in appearance, with very smooth cosmetic features. The formula had desirable dry time, cosmetic feel, tack, emolliency and minimal smell.

These compositions were also checked for antimicrobial efficacy and stability.

| | MIC Results (μg/ml) | | Well Diffusion | Centrifuge Stability |
|---|---|---|---|---|
| Sample | #223 | #502 | % inactivation | % Separation |
| A | 256–128 | 128 | 0 | 0 |
| B | 8 | 8 | 72 | 0 |
| C | 8 | 8 | 32 | 0 |
| D | 8 | 8–4 | 11 | 1 |

The MIC results indicate no inactivation of the CHG by the DMAEMA Q thickener or the emollients. The centrifuge stability was determined by centrifugation of the sample at 3,000 rpm for 30 minutes. The centrifuge was an American Scientific Products, Labofuge B. The vials used to hold the sample were 16 mm diameter-15 ml polypropylene vials from Corning.

The following table shows the "SALCARE SC95" viscosity profile with and without CHG, cleaned and used as received and at varying alcohol/water ratio. The formula are at 2.5% DMAEMA Q solids. Also reported are conductivity results.

The conductivity was determined using a Model 76 Conductivity Meter by Engineered Systems & Designs, Newark, Del. The temperature of the sample was determined and the conductivity meter was adjusted to this temperature. The electrode was immersed in the sample, which was gently stirred. The range on the meter was selected to give a reading of the solution. The electrode was rinsed with Deionized Water between samples.

| Formula | % Ethanol by wt | % CHG | SC95 soln 50% solids | CHG Cleaned DMAEMAQ | 20% Soln | 190 Ethanol | DI Water | Visocity cps | rpm | NaCl μmho | Aqueous equivalent (ppm) |
|---|---|---|---|---|---|---|---|---|---|---|---|
| A  | 35% | 0%    | 3.00 |      | 0.00 | 21.58 | 35.42 | 437,000 | 0.3  | 1010 | 515 |
| B  | 45% | 0%    | 3.00 |      | 0.00 | 27.75 | 29.25 | 437,000 | 0.3  | 780  | 394 |
| C  | 55% | 0%    | 3.00 |      | 0.00 | 33.91 | 23.09 | 437,000 | 0.3  | 550  | 274 |
| D  | 65% | 0%    | 3.00 |      | 0.00 | 40.08 | 16.92 | 356,000 | 0.3  | 430  | 211 |
| E  | 75% | 0%    | 3.00 |      | 0.00 | 46.25 | 10.75 | *       | 0.3  | 110  | 44  |
| F  | 85% | 0%    | 3.00 |      | 0.00 | 52.41 | 4.59  | *       | 0.3  | 50   | 13  |
| G  | 90% | 0%    | 3.00 |      | 0.00 | 55.50 | 1.50  | *       | 0.3  | 50   | 13  |
| H  | 35% | 0%    |      | 1.50 | 0.00 | 22.15 | 36.35 | 468,000 | 0.3  | 750  | 379 |
| I  | 45% | 0%    |      | 1.50 | 0.00 | 28.48 | 30.02 | 468,000 | 0.3  | 620  | 311 |
| J  | 55% | 0%    |      | 1.50 | 0.00 | 34.81 | 23.69 | 468,000 | 0.3  | 440  | 217 |
| K  | 65% | 0%    |      | 1.50 | 0.00 | 41.13 | 17.37 | 468,000 | 0.3  | 330  | 159 |
| L  | 75% | 0%    |      | 1.50 | 0.00 | 47.46 | 11.04 | 412,000 | 0.3  | 240  | 112 |
| M  | 85% | 0%    |      | 1.50 | 0.00 | 53.79 | 4.71  | *       | 0.3  | 10   | 0   |
| N  | 90% | 0%    |      | 1.50 | 0.00 | 56.96 | 1.54  | *       | 0.3  | 10   | 0   |
| O  | 35% | 0.50% | 3.00 |      | 1.58 | 21.47 | 33.95 | 293,000 | 0.3  | 1100 | 562 |
| P  | 45% | 0.50% | 3.00 |      | 1.58 | 27.60 | 27.82 | 312,000 | 0.3  | 960  | 489 |
| Q  | 55% | 0.50% | 3.00 |      | 1.58 | 33.74 | 21.69 | 183,000 | 0.3  | 720  | 363 |
| R  | 60% | 0.50% | 3.00 |      | 1.58 | 36.80 | 18.62 | 60,000  | 0.3  | 600  | 300 |
| S  | 65% | 0.50% | 3.00 |      | 1.58 | 39.87 | 15.55 | 300     | 50.0 | 540  | 269 |
| T  | 75% | 0.50% | 3.00 |      | 1.58 | 46.00 | 9.42  | *       | 0.3  | 250  | 117 |
| U  | 85% | 0.50% | 3.00 |      | 1.58 | 52.14 | 3.28  | *       | 0.3  | 230  | 107 |
| V  | 90% | 0.50% | 3.00 |      | 1.58 | 55.20 | 0.22  | *       | 0.3  | 170  | 75  |
| W  | 35% | 0.50% |      | 1.50 | 1.58 | 22.04 | 34.89 | 406,000 | 0.3  | 810  | 410 |
| X  | 45% | 0.50% |      | 1.50 | 1.58 | 28.33 | 28.59 | 306,000 | 0.3  | 770  | 389 |
| Y  | 55% | 0.50% |      | 1.50 | 1.58 | 34.63 | 22.29 | 168,000 | 0.3  | 620  | 311 |
| Z  | 60% | 0.50% |      | 1.50 | 1.58 | 37.78 | 19.15 | 119,000 | 0.3  | 520  | 258 |
| AA | 65% | 0.50% |      | 1.50 | 1.58 | 40.92 | 16.00 | 1,400   | 20.0 | 480  | 238 |
| BB | 75% | 0.50% |      | 1.50 | 1.58 | 47.22 | 9.70  | *       | 0.3  | 240  | 112 |
| CC | 85% | 0.50% |      | 1.50 | 1.58 | 53.52 | 3.41  | *       | 0.3  | 170  | 75  |
| DD | 90% | 0.50% |      | 1.50 | 1.58 | 56.66 | 0.26  | *       | 0.3  | 150  | 65  |

*Viscosity below limits of viscometer.
Salcare SC 95, Allied Colloids, Inc.
CHG Soln 20.1% w/v, Medichem S.A.
Ethanol 190 Proof, Aaper Alcohol
DI Water, 3 M DI tap
Conductivity Meter Model 76 from Engineered Systems & Designs, 119 Sandy Dr. Newark, DE 19713
The conductance of a body in mho is the reciprocal of the value of its resistance in ohms.

Example 10

Modified Cellulosic Thickeners

The following formulation was prepared by first placing the Klucel in the alcohol/water solvent and stirring occasionally until uniform. Once uniform the emollients cetyl alcohol and phenyl trimethicone were added.

| | |
|---|---|
| 1.0 g | Klucel HF |
| 2.0 g | Cetyl Alcohol |
| 1.0 g | Phenyl trimethicone, Dow Corning 556 |
| 24.0 g | Deionized Water |
| 72.0 g | IPA |

The solution was a viscous clear solution which had a slippery feel when wet. On drying the material had a tendency to ball up on the palms during drying.

| | |
|---|---|
| 1.0 g | Klucel HF |
| 2.0 g | Cetyl Alcohol |
| 1.0 g | Phenyl trimethicone, Dow Corning 556 |
| 24.0 g | Deionized Water |
| 72.0 g | Absolute Ethanol |

The solution was a viscous opaque solution which had a slippery feel when wet. On drying the material had a tendency to ball up on the palms during drying.

While in accordance with the patent statutes, description of the preferred weight fractions, processing conditions, and product usages have been provided, the scope of the invention is not intended to be limited thereto or thereby. Various modifications and alterations of the present invention will be apparent to those skilled in the art without departing from the scope and spirit of the present invention. The Examples described in this application are illustrative of the possibilities of varying the type, quantity and ratio of composition as well as the methods for making formulations of the present invention. All patents, patent applications, and publications cited herein are incorporated by reference in their entirety, as if individually incorporated.

What is claimed is:

1. An antimicrobial hydroalcoholic composition comprising:
   (a) a hydroalcoholic solvent system comprising a C1-C4 alcohol and water in a weight ratio of C1-C4 alcohol to water of at least 60:40; wherein the C1-C4 alcohol is present in the composition in an amount of at least 60% by weight, based on the total weight of the composition;
   (b) a thickener system consisting essentially of at least one associative polymeric thickener that is solid at ambient temperature, is cationic or nonionic, thickens the hydroalcoholic solvent system, and comprises greater than two hydrophobic chains of greater than 16 carbon atoms per polymer molecule; wherein the associative polymeric thickener has a number average molecular weight of at least 20,000; wherein the thickener system is present in an amount of at least 0.5% by weight, based on the total weight of the composition; and
   (c) a secondary antimicrobial agent.

2. The composition of claim 1 which has a pH of at least 5.

3. The composition of claim 1 wherein the associative polymeric thickener is cationic.

4. The composition of claim 1 wherein the associative polymeric thickener is nonionic.

5. The composition of claim 1 wherein the polymeric thickener is selected such that the composition has a viscosity of at least 50,000 centipoise at 23° C.

6. The composition of claim 1 wherein the thickener system is present in an amount of greater than about 2% by weight, based on the total weight of the composition.

7. The composition of claim 1 wherein the associative polymeric thickener is soluble in the hydroalcoholic solvent system.

8. The composition of claim 1 further comprising a pharmaceutical agent.

9. The composition of claim 1 which is substantially non-tacky.

10. The composition of claim 1 which is a lotion.

11. The composition of claim 10 which is a hand antisepsis lotion.

12. The composition of claim 11 which is substantially nontacky.

13. The composition of claim 1 that is a presurgical scrub.

14. The composition of claim 13 wherein the hydrophobic group is a grafted side chain.

15. The composition of claim 1 wherein the hydrophobic group is a grafted side chain.

16. The composition of claim 1 wherein the associative polymeric thickener is swellable.

17. The composition of claim 1 which is a foam.

18. An antimicrobial hydroalcoholic composition comprising:
   (a) a hydroalcoholic solvent system comprising a C1-C4 alcohol and water in a weight ratio of C1-C4 alcohol to water of at least 60:40; wherein the C1-C4 alcohol is present in the composition in an amount of at least 60% by weight, based on the total weight of the composition;
   (b) a thickener system comprising at least one associative polymeric thickener that is solid at ambient temperature, thickens the hydroalcoholic solvent system, and comprises greater than two hydrophobic chains of greater than 16 carbon atoms per polymer molecule; wherein the associative polymeric thickener is cationic or nonionic and has a number average molecular weight of at least 20,000; wherein the thickener system is present in an amount of at least 0.5% by weight, based on the total weight of the composition; and
   (c) a secondary antimicrobial agent.

19. The composition of claim 18 which is a lotion.

20. The composition of claim 18 which is a foam.

21. The composition of claim 18 further comprising a cationic polymeric thickener that is not an associative thickener.

22. The composition of claim 18 further comprising a nonionic polymeric thickener that is not an associative thickener.

23. The composition of claim 18 further comprising a swellable polymeric thickener.

24. The composition of claim 18 further comprising a polyether/polysiloxane copolymer.

25. The composition of claim 24 which is a foam or a mousse.

26. An antimicrobial hydroalcoholic composition comprising:
   (a) a hydroalcoholic solvent system comprising a C1-C4 alcohol and water in a weight ratio of C1-C4 alcohol to water of at least 60:40; wherein the C1-C4 alcohol is present in the composition in an amount of at least 60% by weight, based on the total weight of the composition;
   (b) a thickener system comprising at least one associative polymeric thickener that is solid at ambient temperature, thickens the hydroalcoholic solvent system, has a number average molecular weight of at least 20,000, and comprises greater than two hydrophobic chains of greater than 16 carbon atoms per polymer molecule; wherein the associative polymeric thickener is cationic or nonionic and is present in an amount such that the composition has a viscosity of at least 2,000 centipoise at 23° C.; and
   (c) a secondary antimicrobial agent.

27. The composition of claim 26 wherein the associative polymeric thickener is present in an amount such that the composition has a viscosity of at least 4,000 centipoise at 23° C.

28. The composition of claim 26 which is a lotion.

29. The composition of claim 26 which is a foam.

30. The composition of claim 26 further comprising a cationic polymeric thickener that is not an associative thickener.

31. The composition of claim 26 further comprising a nonionic polymeric thickener that is not an associative thickener.

32. The composition of claim 26 further comprising a swellable polymeric thickener.

33. The composition of claim 26 further comprising a polyether/polysiloxane copolymer.

34. The composition of claim 33 which is a foam or a mousse.

35. A hydroalcoholic composition comprising:
   (a) a hydroalcoholic solvent system comprising a C1-C4 alcohol and water in a weight ratio of C1-C4 alcohol to water of at least 60:40; wherein the C1-C4 alcohol is present in the composition in an amount of at least 60% by weight, based on the total weight of the composition;
   (b) a thickener system consisting essentially of at least one associative polymeric thickener that is solid at ambient temperature, is cationic or nonionic, thickens the hydroalcoholic solvent system, and comprises greater than two hydrophobic chains of greater than 16 carbon atoms per polymer molecule; wherein the associative polymeric thickener has a number average molecular weight of at least 20,000; wherein the thickener system is present in an amount of at least 0.5% by weight, based on the total weight of the composition; and (c) a secondary agent selected from the group consisting of at least one of an antimicrobial agent, a pharmaceutical agent, a skin barrier, and an antifungal agent.

36. The composition of claim 35 which is an acne medication.

37. A hydroalcoholic composition comprising:
(a) a hydroalcoholic solvent system comprising a C1-C4 alcohol and water in a weight ratio of C1-C4 alcohol to water of at least 60:40; wherein the C1-C4 alcohol is present in the composition in an amount of at least 60% by weight, based on the total weight of the composition;
(b) a thickener system comprising at least one associative polymeric thickener that is solid at ambient temperature, thickens the hydroalcoholic solvent system, and comprises greater than two hydrophobic chains of greater than 16 carbon atoms per polymer molecule; wherein the associative polymeric thickener is cationic or nonionic and has a number average molecular weight of at least 20,000; wherein the thickener system is present in an amount of at least 0.5% by weight, based on the total weight of the composition; and
(c) a secondary agent selected from the group consisting of at least one of an antimicrobial agent, a pharmaceutical agent, a skin barrier, and an antifungal agent.

38. The composition of claim 37 which is an acne medication.

39. A hydroalcoholic composition comprising:
(a) a hydroalcoholic solvent system comprising a C1-C4 alcohol and water in a weight ratio of C1-C4 alcohol to water of at least 60:40; wherein the C1-C4 alcohol is present in the composition in an amount of at least 60% by weight, based on the total weight of the composition;
(b) a thickener system comprising at least one associative polymeric thickener that is solid at ambient temperature, thickens the hydroalcoholic solvent system, has a number average molecular weight of at least 20,000, and comprises greater than two hydrophobic chains of greater than 16 carbon atoms per polymer molecule; wherein the associative polymeric thickener is cationic or nonionic and is present in an amount such that the composition has a viscosity of at least 2,000 centipoise at 23° C.; and
(c) a secondary agent selected from the group consisting of at least one of an antimicrobial agent, a pharmaceutical agent, a skin barrier, and an antifungal agent.

40. The composition of claim 39 which is an acne medication.

41. An antimicrobial hydroalcoholic composition comprising:
(a) a hydroalcoholic solvent system comprising a C1-C4 alcohol and water in a weight ratio of C1-C4 alcohol to water of about 60:40 to about 95:5; wherein the C1-C4 alcohol is present in the composition in an amount of at least 60% by weight, based on the total weight of the composition;
(b) a thickener system comprising one or more associative polymeric thickeners, at least one of which is solid at ambient temperature, has a number average molecular weight of at least 20,000, thickens the hydroalcoholic solvent system, is nonionic, and comprises greater than two hydrophobic chains of greater than 16 carbon atoms per polymer molecule; and
(c) a secondary antimicrobial agent.

42. The composition of claim 41 wherein the nonionic associative polymeric thickener is present in an amount such that the composition has a viscosity of at least 2,000 centipoise at 23° C.

43. The composition of claim 42 wherein the thickener system is present in an amount of at least 0.5% by weight, based on the total weight of the composition.

44. The composition of claim 41 wherein the nonionic associative polymeric thickener is derived from ethylenically unsaturated monomers.

45. The composition of claim 44 wherein the nonionic associative polymeric thickener is derived from ethylenically unsaturated monomers selected from the group of acrylates, acrylamides, vinyl lactams, vinyl acetate and its hydrolyzed derivatives, methyl vinyl ethers, styrene, and acrylonitrile.

46. The composition of claim 41 wherein the nonionic associative polymeric thickener is selected such that the composition has a viscosity of at least 4,000 centipoise at 23° C.

47. The composition of claim 41 wherein the nonionic associative polymeric thickener system is present in an amount of less than 10% by weight, based on the total weight of the composition.

48. The composition of claim 41 wherein the thickener system is present in an amount of greater than 2% by weight, based on the total weight of the composition.

49. The composition of claim 41 wherein the secondary antimicrobial agent is selected from the group of chlorhexidine salts, iodine, triclosan, parachlorometaxylenol, and mixtures thereof.

50. The composition of claim 41 further comprising at least one emollient.

51. The composition of claim 50 wherein at least one emollient is present in an amount of about 1% to about 30%, based on the total weight of the composition.

52. The composition of claim 51 wherein the emollient is selected from the group of a wax, an oil, a humectant, and mixtures thereof.

53. The composition of claim 41 which is stable and does not separate more than 10% by volume when centrifuged for 30 minutes at 1545×g.

54. The composition of claim 41 further comprising a pharmaceutical agent.

55. The composition of claim 41 which is a lotion.

56. The composition of claim 55 wherein the lotion is in the form of an emulsion.

57. The composition of claim 41 which is a foam.

58. The composition of claim 41 further comprising at least one fragrance.

59. A method of disinfecting skin, the method comprising applying to skin a composition of claim 1.

60. The method of claim 59 comprising dispensing the composition in a discrete and substantially uniform amount.

61. A method of disinfecting skin, the method comprising applying to skin a composition of claim 18.

62. The method of claim 61 comprising dispensing the composition in a discrete and substantially uniform amount.

63. A method of disinfecting skin, the method comprising applying to skin a composition of claim 26.

64. The method of claim 63 comprising dispensing the composition in a discrete and substantially uniform amount.

65. A method of disinfecting skin, the method comprising applying to skin a composition of claim 41.

66. The method of claim 65 comprising dispensing the composition in a discrete and substantially uniform amount.

67. A method of delivering an agent, the method comprising applying to skin a composition of claim 35.

68. The method of claim 67 comprising dispensing the composition in a discrete and substantially uniform amount.

69. A method of delivering an agent, the method comprising applying to skin a composition of claim 37.

70. The method of claim 69 comprising dispensing the composition in a discrete and substantially uniform amount.

71. A method of delivering an agent, the method comprising applying to skin a composition of claim 39.

72. The method of claim 71 comprising dispensing the composition in a discrete and substantially uniform amount.

73. A method of delivering an agent, the method comprising applying to skin a composition of claim 41.

74. The method of claim 73 comprising dispensing the composition in a discrete and substantially uniform amount.

* * * * *

UNITED STATES PATENT AND TRADEMARK OFFICE
CERTIFICATE OF CORRECTION

PATENT NO. : 8,062,649 B2
APPLICATION NO. : 10/463497
DATED : November 22, 2011
INVENTOR(S) : Robert A Asmus It is certified that error appears in the above-identified patent and that said Letters Patent is hereby corrected as shown below:

Title page, Column 1 (Assignee)
Line 1-2, Delete "St Paul, MN" and insert -- St. Paul, MN --, therefor.

Page 2, Column 2 (Other Publications)
Line 6, Delete "CEKAQUAT" and insert -- CELAQUAT --, therefor.

Page 3, Column 1 (Other Publications)
Line 4, Delete "Pharmaceutcal" and insert -- Pharmaceutical --, therefor.
Line 24, Delete "Von" and insert -- Van --, therefor.
Line 31, Delete "Hgy" and insert -- Hyg --, therefor.
Line 58, Delete "((1989)." and insert -- (1989). --, therefor.

Page 3, Column 2 (Other Publications)
Line 22, Delete "4thy" and insert -- 4th --, therefor.

Column 14
Line 18, Delete "4amine," and insert -- 4-amine, --, therefor.
Line 33, Delete "flecamide);" and insert -- flecainide); --, therefor.

Column 15-16
Lines 64-67 (Col. 15) through lines 1-3 (Col. 16) Below "and the like."
 delete "The compositions of the present invention can be dispensed in a
 discreet, substantially uniform amount using the dispensers disclosed in
 Applicants' Assignees' Copending U.S. patent application Ser. Nos.
 08/668,198, filed Jun. 21, 1996, entitled "Dispenser for Antimicrobial
 Liquids" and 08/668,270, filed Jun. 21, 1996 entitled "Drip Resistant Nozzle
 for a Dispenser"." and insert the same below "and the like." on Col. 15, Line
 64 as a new paragraph.

Signed and Sealed this
Seventeenth Day of July, 2012

David J. Kappos
*Director of the United States Patent and Trademark Office*

CERTIFICATE OF CORRECTION (continued)
U.S. Pat. No. 8,062,649 B2

Column 16
Line 28, Delete "LVDV-I+" and insert -- LVDV-I$^+$ --, therefor.

Column 18
Line 25, Delete "Arlamole" and insert -- Arlamol --, therefor.

Column 19
Line 47, Delete "Compostions" and insert -- Compositions --, therefor.

Column 20
Line 17, Delete "OT" and insert -- QT --, therefor.

Column 21-22
Line 8, Delete "trimethylammoniium" and insert -- trimethylammonium --, therefor.
Line 10, Delete "ethylacylate" and insert -- ethylacrylate --, therefor.

Column 23
Line 4, Delete "0" and insert -- O --, therefor.

Column 25-26
Line 15 (Approx.), Delete "CHG" and insert the same on Line 2, above "20%" in the Table.
Line 15 (Approx.), Delete "NaCl" and insert the same on Line 2, below "Aqueous" in the Table.
Line 16 (Approx.), Delete "Visocity" and insert -- Viscosity --, therefor.

Column 27
Line 50, In Claim 14, delete "13" and insert -- 1 --, therefor.